(12) United States Patent
Yamaya

(10) Patent No.: US 11,064,866 B2
(45) Date of Patent: Jul. 20, 2021

(54) ENDOSCOPE COVER, ENDOSCOPE, COVER UNIT, AND ENDOSCOPE UNIT

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 487 days.

(21) Appl. No.: 16/032,526

(22) Filed: Jul. 11, 2018

(65) Prior Publication Data

US 2018/0317741 A1 Nov. 8, 2018

Related U.S. Application Data

(63) Continuation of application No. PCT/JP2017/000669, filed on Jan. 11, 2017.

(30) Foreign Application Priority Data

Jan. 14, 2016 (JP) .............................. JP2016-005541

(51) Int. Cl.
| | |
|---|---|
| *A61B 1/00* | (2006.01) |
| *A61B 1/05* | (2006.01) |
| *A61B 1/12* | (2006.01) |
| *G02B 23/24* | (2006.01) |
| *A61B 1/06* | (2006.01) |

(52) U.S. Cl.
CPC ........ *A61B 1/0008* (2013.01); *A61B 1/00062* (2013.01); *A61B 1/00089* (2013.01); *A61B 1/00098* (2013.01); *A61B 1/00101* (2013.01); *A61B 1/00135* (2013.01); *A61B 1/00137* (2013.01); *A61B 1/05* (2013.01); *A61B 1/0676* (2013.01); *A61B 1/122* (2013.01);
(Continued)

(58) Field of Classification Search
None
See application file for complete search history.

(56) References Cited

U.S. PATENT DOCUMENTS 5,569,157 A * 10/1996 Nakazawa ........... A61B 1/0008
600/104
5,707,344 A 1/1998 Nakazawa et al.
(Continued)

FOREIGN PATENT DOCUMENTS

| JP | 8-243071 A | 9/1996 |
|---|---|---|
| JP | H10-127578 A | 5/1998 |

(Continued)

OTHER PUBLICATIONS

Supplementary Extended European Search Report dated Aug. 16, 2019 received in 17738446.8.
(Continued)

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope cover that is to be attached to a distal framing portion of an endoscope, includes: a cover main body having an annular portion configured to surround a periphery of the distal framing portion; a fragile portion provided in the annular portion of the cover main body, having a mechanical strength lower than a rest of the annular portion.

12 Claims, 29 Drawing Sheets

(52) U.S. Cl.
CPC ......... *G02B 23/24* (2013.01); *G02B 23/2476* (2013.01); *A61B 1/00142* (2013.01)

(56) References Cited

U.S. PATENT DOCUMENTS

| | | | | |
|---|---|---|---|---|
| 5,730,701 | A * | 3/1998 | Furukawa | A61B 1/0008 600/121 |
| 5,860,913 | A * | 1/1999 | Yamaya | A61B 1/00091 600/121 |
| 6,605,033 | B1 * | 8/2003 | Matsuno | A61B 1/00098 600/106 |
| 2001/0018550 | A1 * | 8/2001 | Boebel | A61B 1/018 600/107 |
| 2002/0087100 | A1 * | 7/2002 | Onuki | A61B 1/00098 600/585 |
| 2004/0049095 | A1 * | 3/2004 | Goto | A61B 1/018 600/107 |
| 2005/0101836 | A1 * | 5/2005 | Onuki | A61B 1/00137 600/104 |
| 2007/0118019 | A1 * | 5/2007 | Mitani | A61B 1/00098 600/176 |
| 2007/0246506 | A1 * | 10/2007 | Hamazaki | A61B 1/00101 227/175.1 |
| 2007/0249898 | A1 * | 10/2007 | Otawara | A61B 1/00098 600/107 |
| 2008/0021269 | A1 * | 1/2008 | Tinkham | A61B 1/00098 600/104 |
| 2010/0210905 | A1 * | 8/2010 | Takeuchi | A61B 1/00128 600/110 |
| 2015/0230697 | A1 * | 8/2015 | Phee | A61B 1/05 600/106 |

FOREIGN PATENT DOCUMENTS

| | | |
|---|---|---|
| JP | 2003-102668 A | 4/2003 |
| JP | 2007-289434 A | 11/2007 |
| WO | WO 2013/084561 A1 | 6/2013 |

OTHER PUBLICATIONS

English translation of International Preliminary Report on Patentability dated Jul. 26, 2018 together with the Written Opinion received in related International Application No. PCT/JP2017/000669.

International Search Report dated Mar. 21, 2017 issued in PCT/JP2017/000669.

* cited by examiner

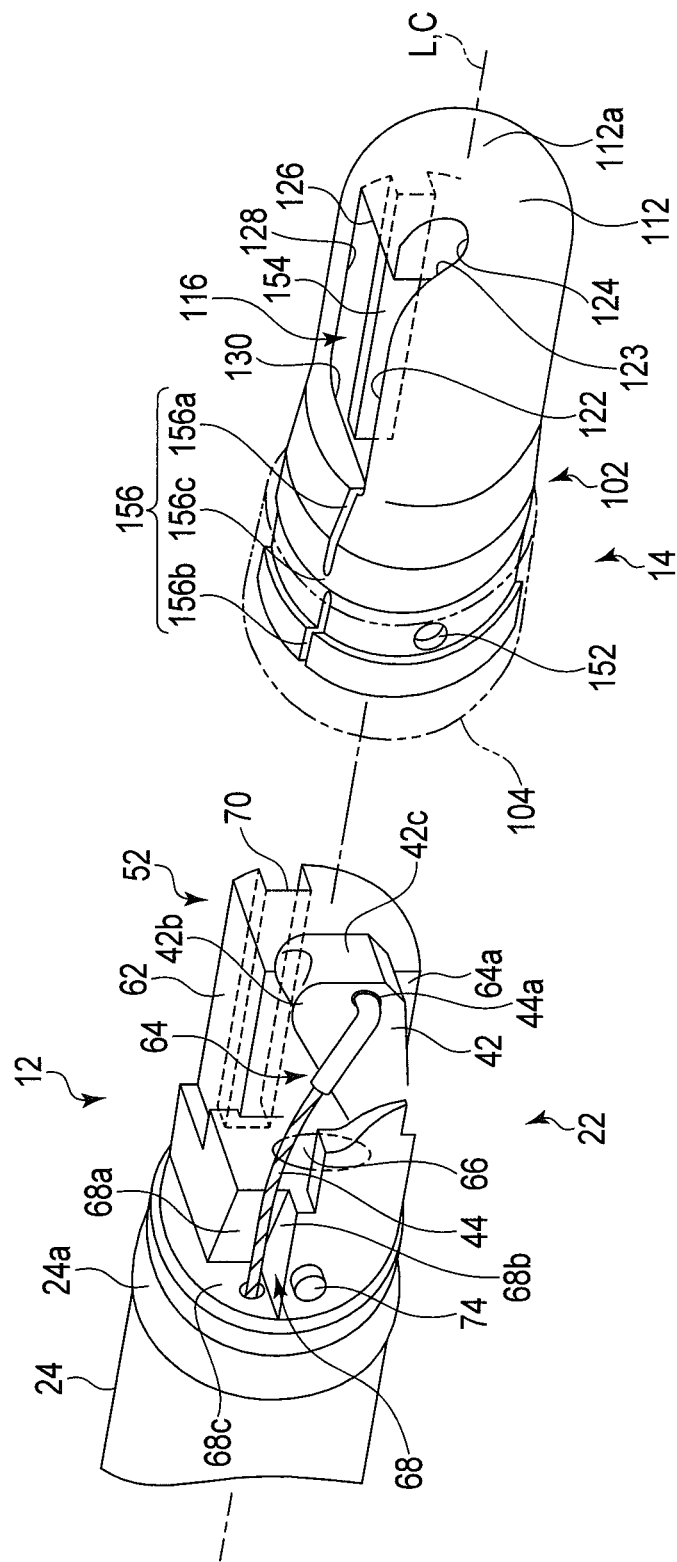
F I G. 6

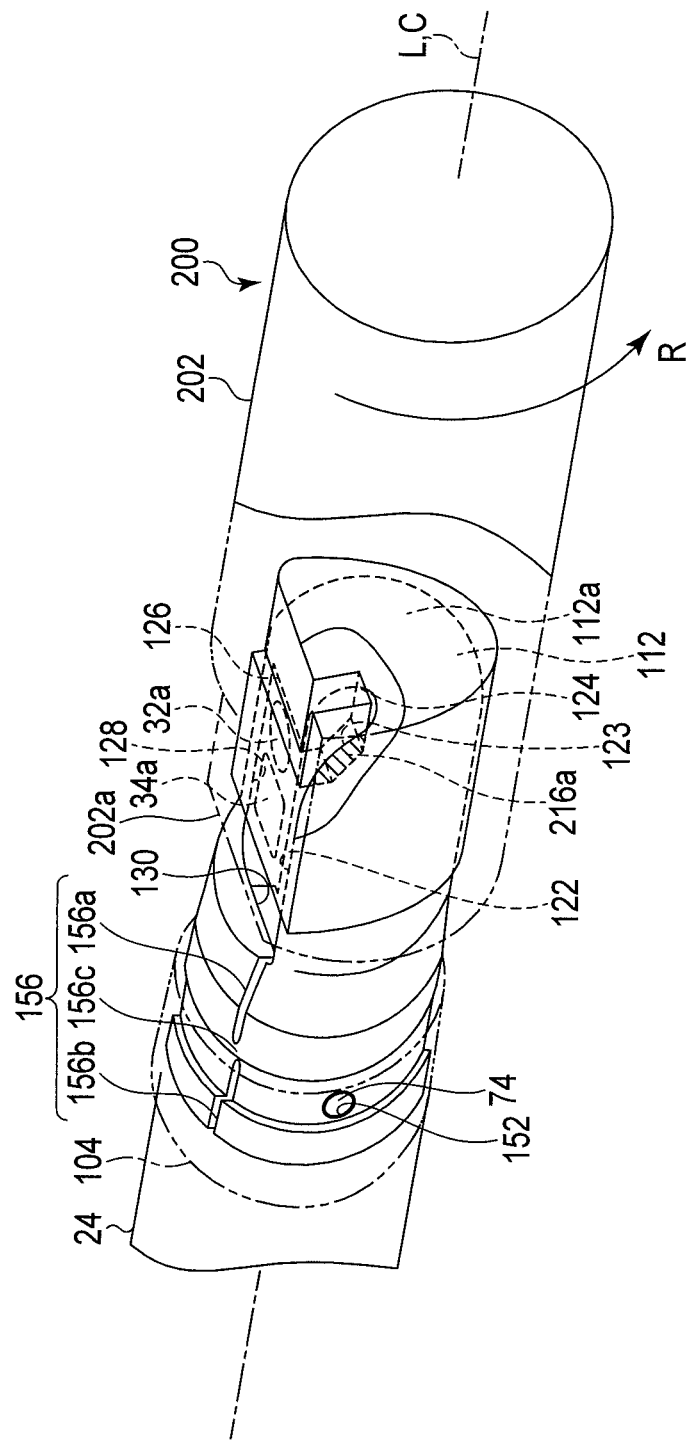
F I G. 12B

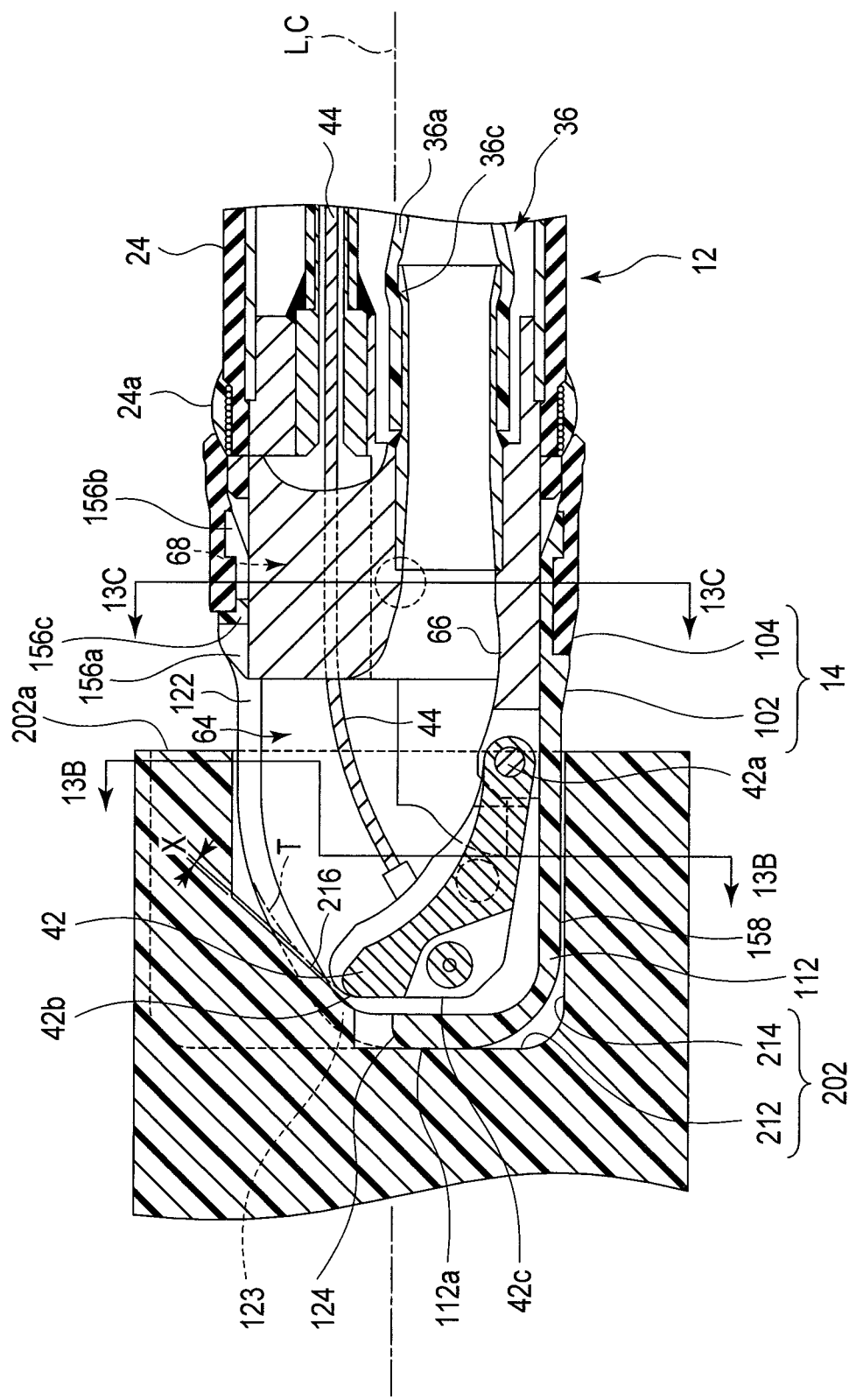
F I G. 13A

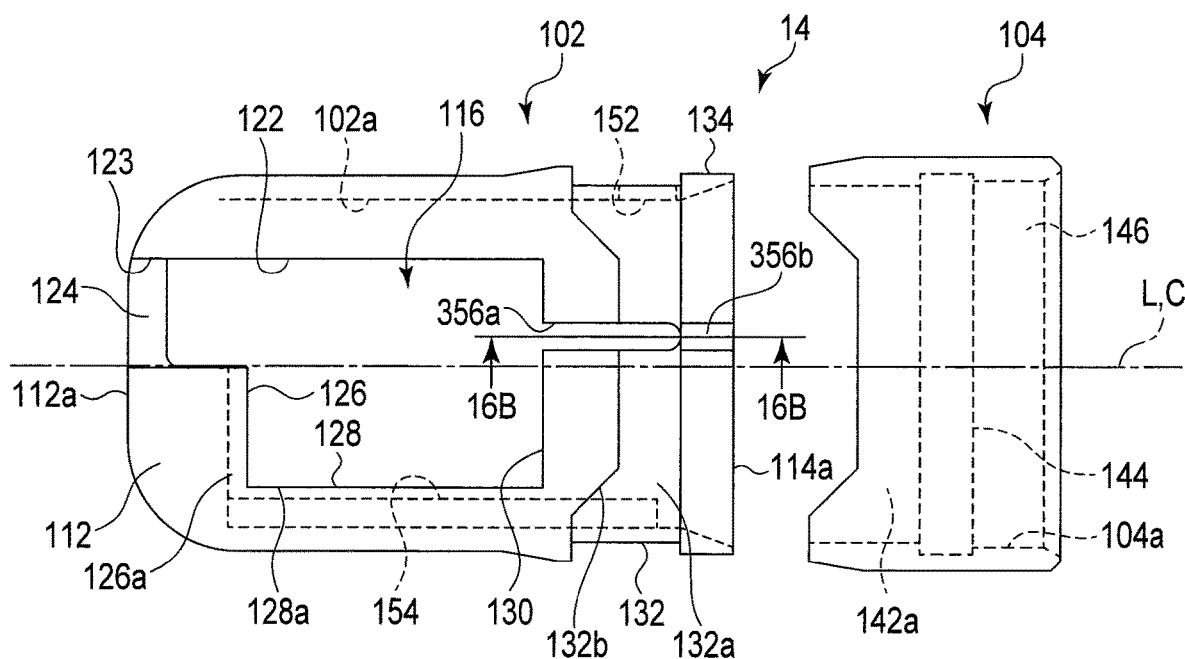
F I G. 16A
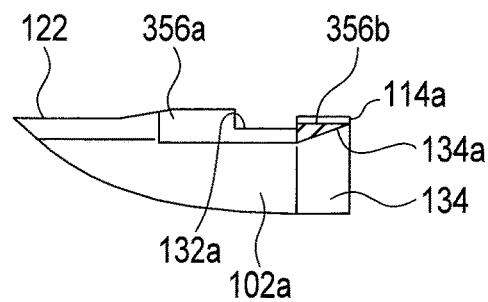
F I G. 16B

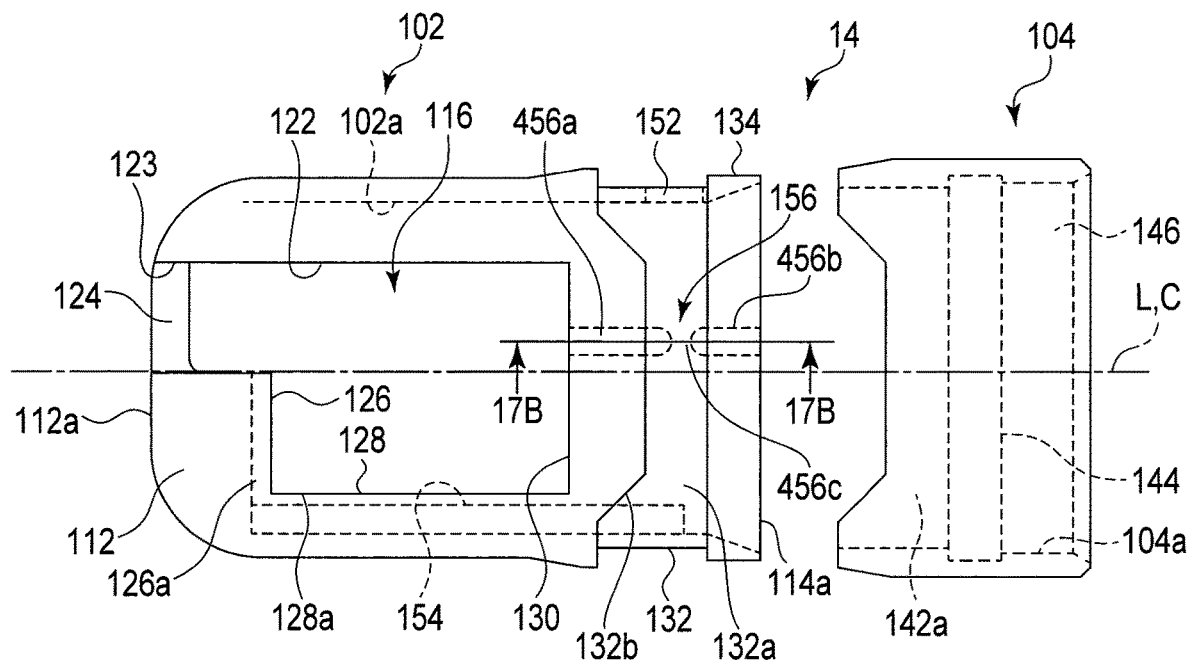
F I G. 17A
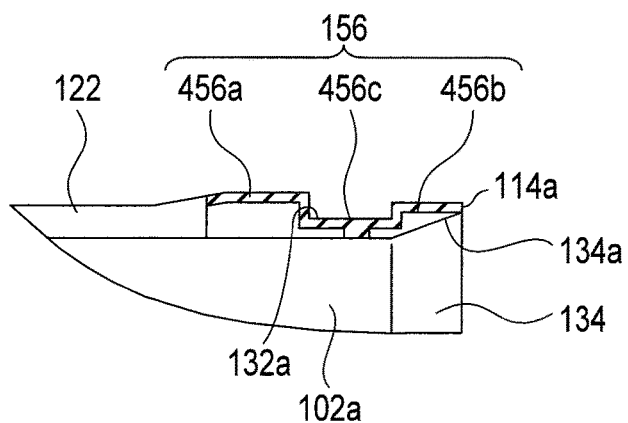
F I G. 17B

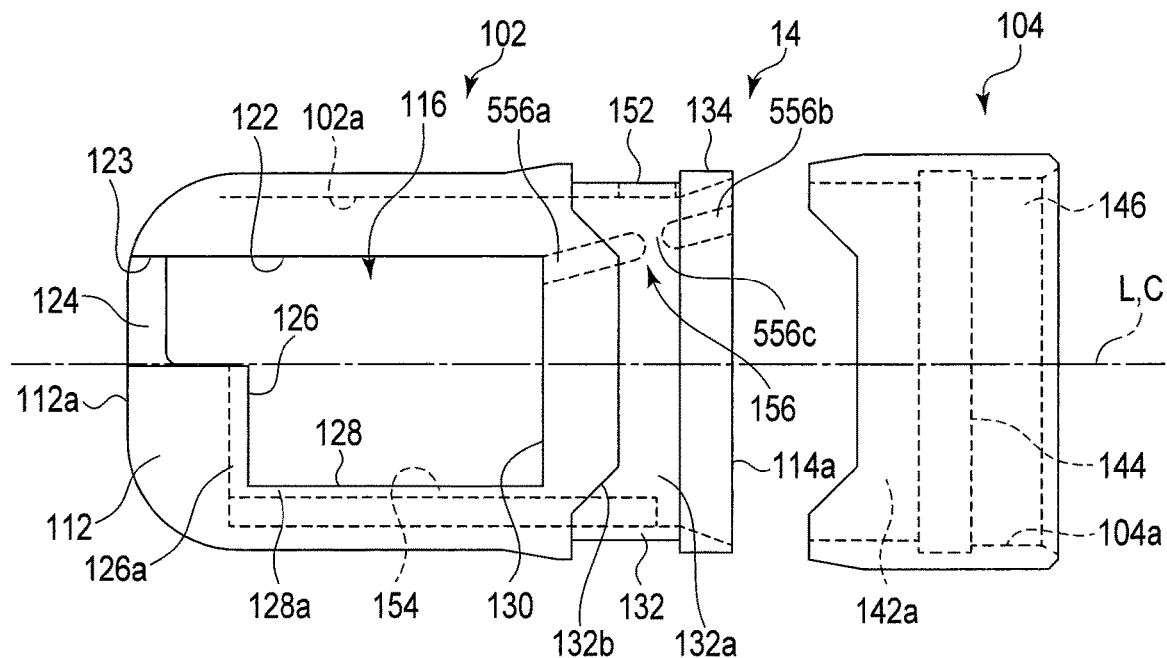
F I G. 18
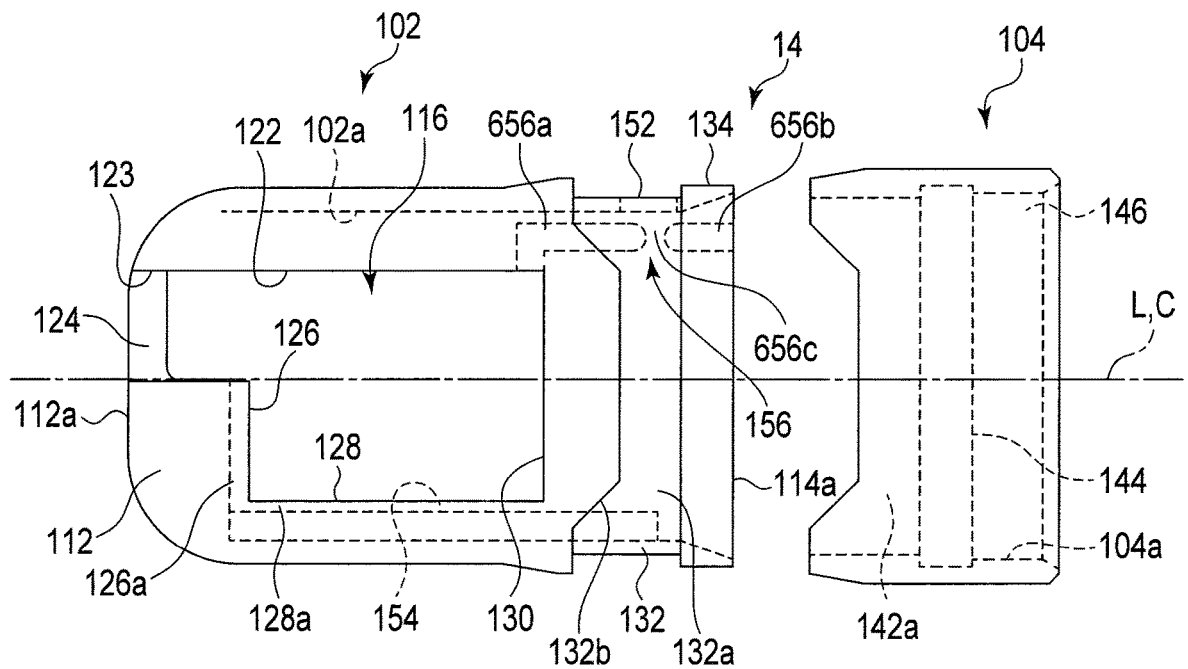
F I G. 19

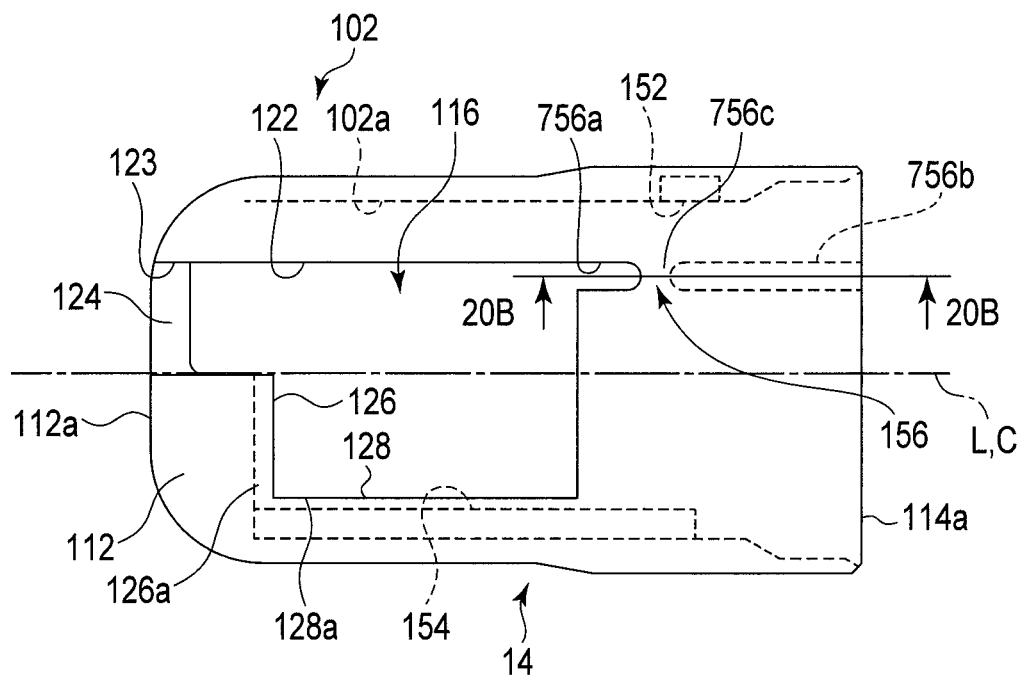
F I G. 20A
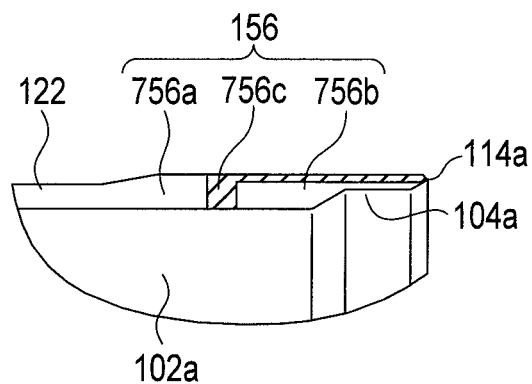
F I G. 20B

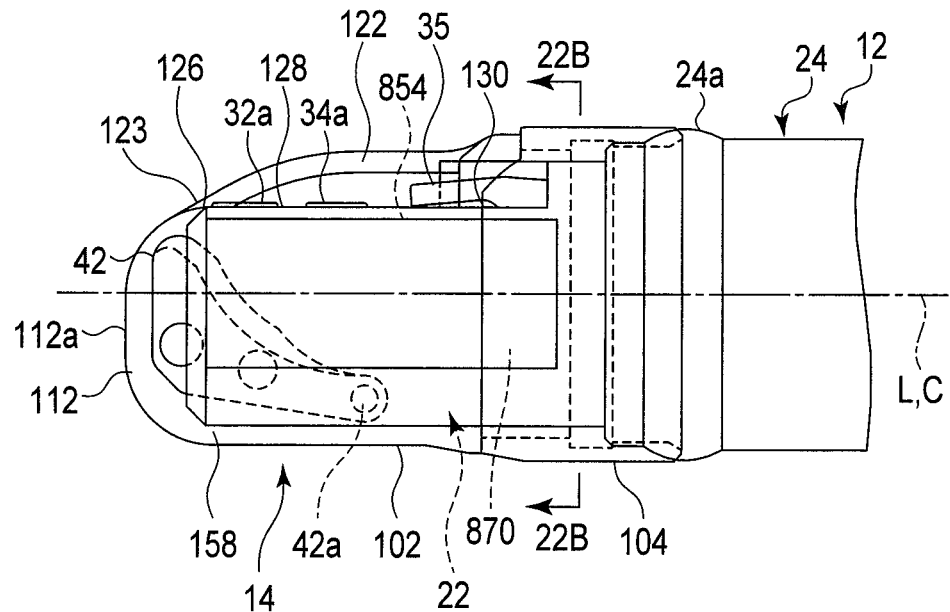
F I G. 22A
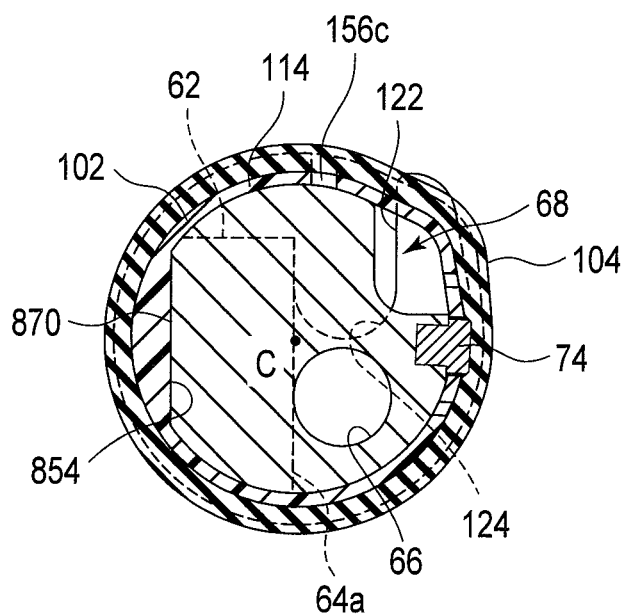
F I G. 22B

ENDOSCOPE COVER, ENDOSCOPE, COVER UNIT, AND ENDOSCOPE UNIT

CROSS-REFERENCE TO RELATED APPLICATIONS

This application is a Continuation Application of PCT Application No. PCT/JP2017/000669, filed Jan. 11, 2017 and based upon and claiming the benefit of priority from prior Japanese Patent Application No. 2016-005541, filed Jan. 14, 2016, the entire contents of all of which are incorporated herein by reference.

BACKGROUND OF THE INVENTION

1. Field of Invention

This invention relates to an endoscope cover that is to be attached to a distal framing portion of an insertion section of an endoscope, an endoscope that includes the endoscope cover, a cover unit, and an endoscope unit.

2. Description of Related Art

Jpn. Pat. Appin. KOKAI Publication No. 2003-102668, for example, discloses a cover that is to be attached to a distal framing portion of an insertion section of an endoscope. The cover is removed by tearing along a groove formed from an edge at its proximal end to its distal end. For the removal of the cover from the distal framing portion, the tearing of the cover from the proximal edge toward the distal side may be performed using a tool or fingers.

BRIEF SUMMARY OF THE INVENTION

According to one aspect of the present invention, an endoscope cover that is to be attached to a distal framing portion of an insertion section of an endoscope, includes: a cover main body that is to be attached to the distal framing portion along a longitudinal axis of the insertion section, the cover main body having an annular portion configured to surround a periphery of the distal framing portion; a fragile portion at least a part of which is provided in the annular portion of the cover main body, the fragile portion having a mechanical strength lower than a rest of the annular portion; and a restriction portion configured to regulate movement of the cover main body around the longitudinal axis with respect to the distal framing portion when an intended stress is applied to the cover main body around the longitudinal axis with the cover main body attached to the distal framing portion and the fragile portion is broken.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 6 is a schematic perspective view showing a state in which the endoscope cover is being attached to the distal framing portion of the endoscope according to the first embodiment.

FIG. 12B is a schematic perspective view showing a state in which the jig has been engaged with the endoscope cover to remove the cover from the distal framing portion of the endoscope according to the first embodiment.

FIG. 13A is a schematic longitudinal sectional view showing a state in which the jig has been engaged with the endoscope cover to remove the cover from the distal framing portion of the endoscope according to the first embodiment.

FIG. 16A is a schematic view showing a state in which an endoscope cover that is to be attached to the distal framing portion of the endoscope according to a modification (first modification) of the first embodiment is disassembled.

FIG. 16B is a schematic longitudinal sectional view of the endoscope cover that is to be attached to the distal framing portion of the endoscope according to the modification (first modification) of the first embodiment, taken along the line 16B-16B in FIG. 16A.

FIG. 17A is a schematic view showing a state in which an endoscope cover that is to be attached to the distal framing portion of the endoscope according to a modification (second modification) of the first embodiment is disassembled.

FIG. 17B is a schematic longitudinal sectional view of the endoscope cover that is to be attached to the distal framing portion of the endoscope according to the modification (second modification) of the first embodiment, taken along the line 17B-17B in FIG. 17A.

FIG. 18 is a schematic view showing a state in which an endoscope cover that is to be attached to the distal framing portion of the endoscope according to a modification (third modification) of the first embodiment is disassembled.

FIG. 19 is a schematic view showing a state in which an endoscope cover that is to be attached to the distal framing portion of the endoscope according to a modification (fourth modification) of the first embodiment is disassembled.

FIG. 20A is a schematic view showing the endoscope cover that is to be attached to the distal framing portion of the endoscope according to a modification (fifth modification) of the first embodiment.

FIG. 20B is a schematic longitudinal sectional view of the endoscope cover that is to be attached to the distal framing portion of the endoscope according to the modification (fifth modification) of the first embodiment, taken along the line 20B-20B in FIG. 20A.

FIG. 22A is a schematic side view showing a state of the endoscope cover that has been attached to the distal framing portion of the endoscope according to the second embodiment.

FIG. 22B is a schematic cross sectional view showing the state of the endoscope cover that has been attached to the distal framing portion of the endoscope according to the second embodiment, taken along the line 22B-22B in FIG. 22A.

DETAILED DESCRIPTION OF THE INVENTION

Embodiments of the present invention will be described below with reference to the drawings.

The first embodiment is described with reference to FIGS. 1 to 14.

Figure 1:
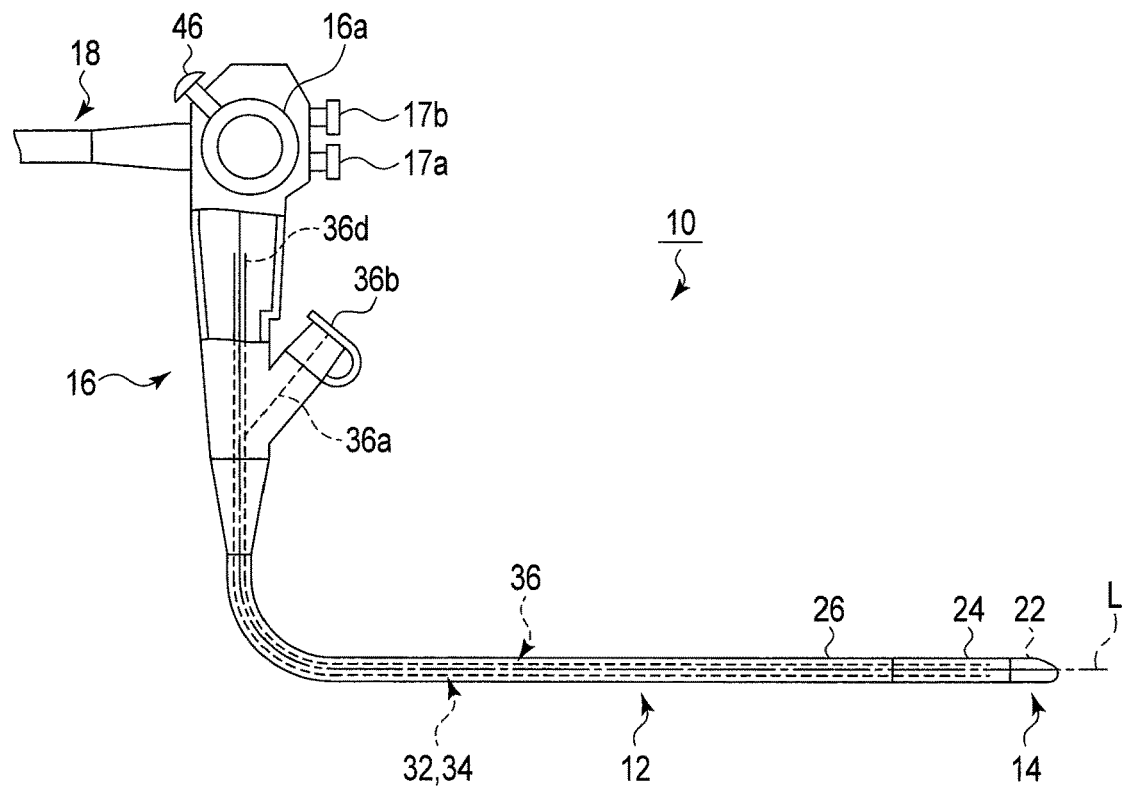
FIG. 1 is a schematic view of an endoscope according to first and third embodiments.
Figure 2A:
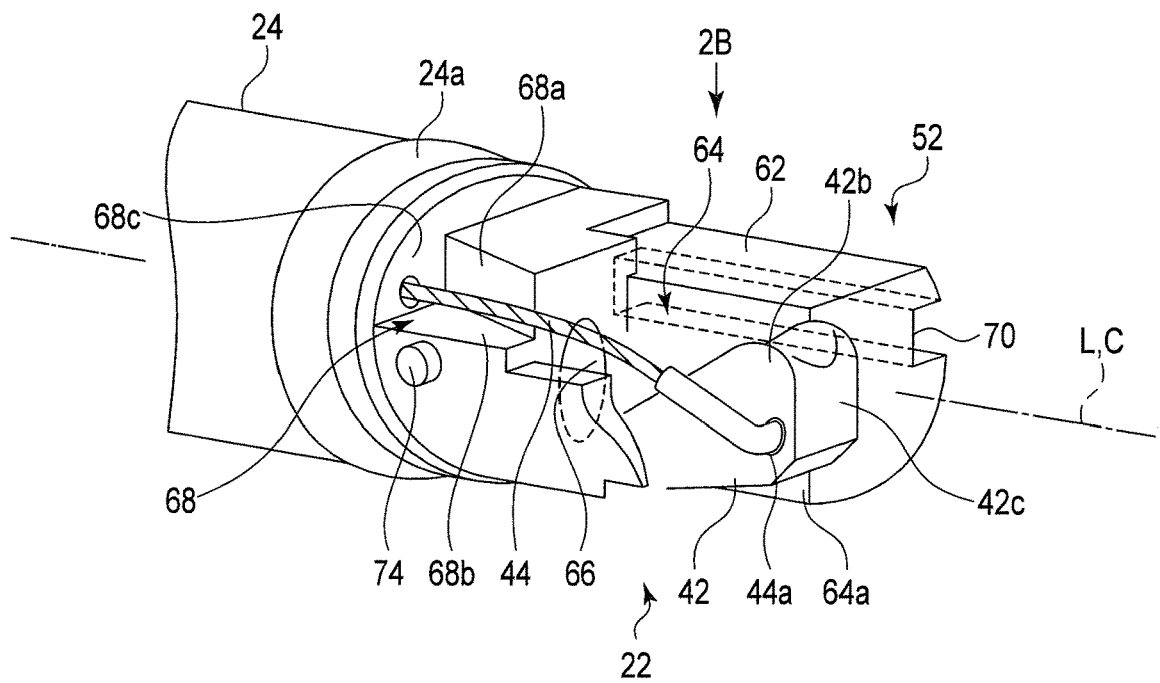
FIG. 2A is a schematic perspective view showing a distal framing portion of the endoscope according to the first embodiment.
Figure 2B:
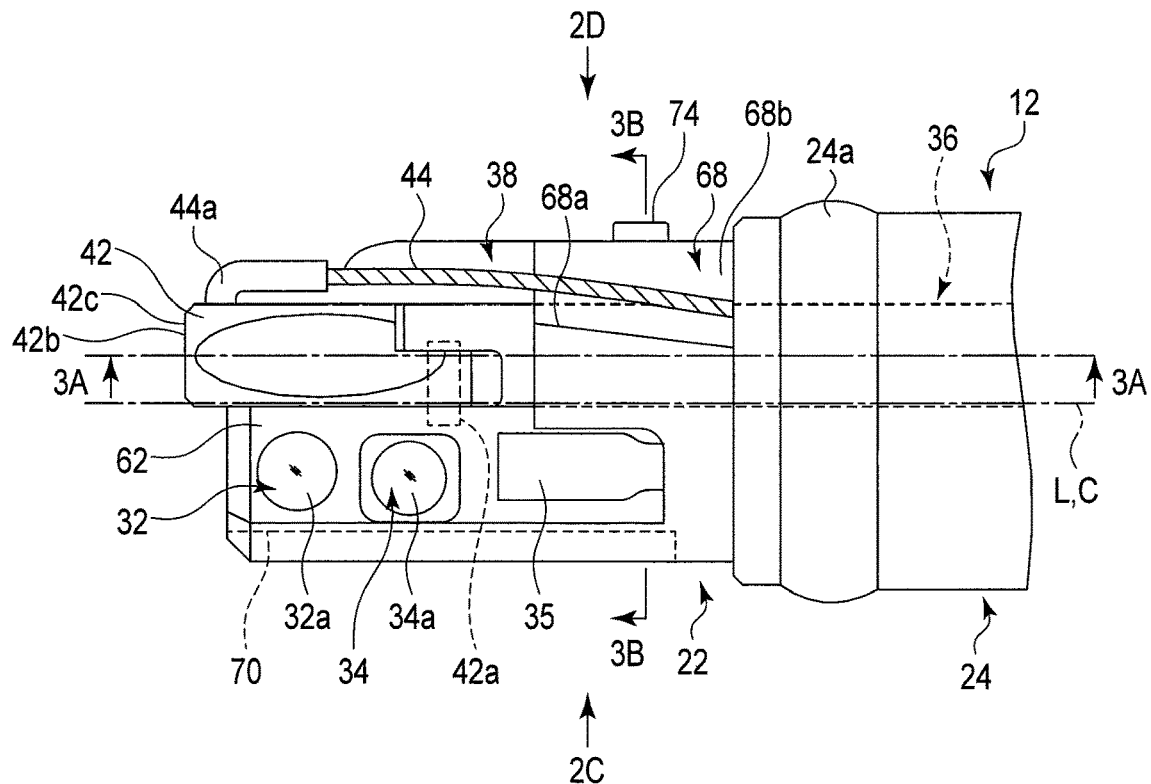
FIG. 2B is a view of the distal framing portion of the endoscope according to the first embodiment viewed from an arrow 2B side in FIG. 2A.
Figure 2C:
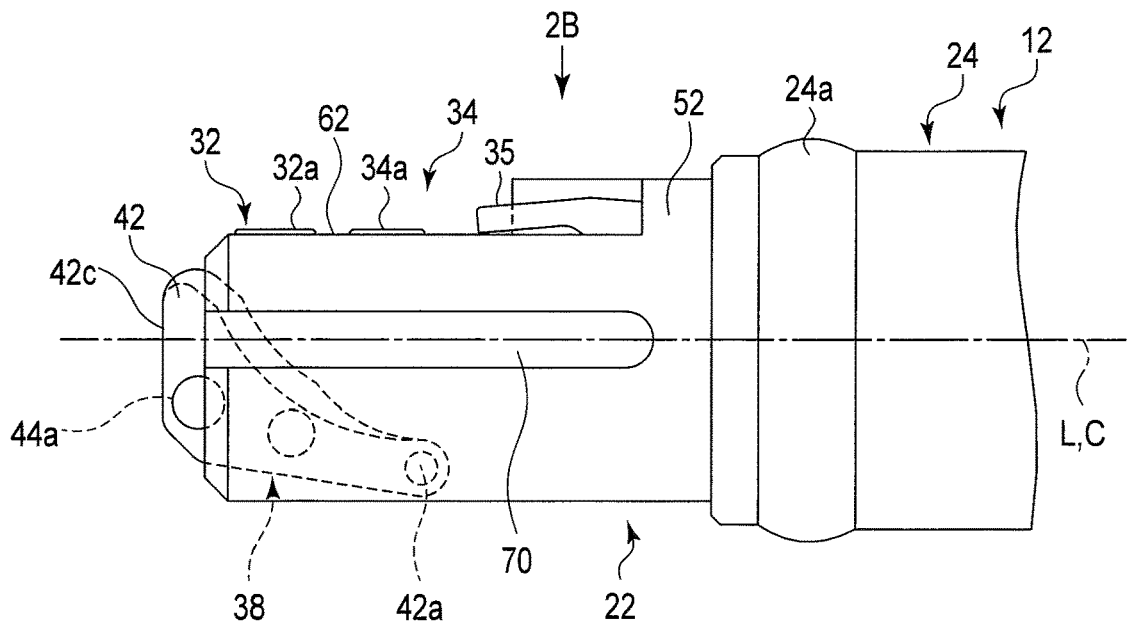
FIG. 2C is a view of the distal framing portion of the endoscope according to the first embodiment viewed from an arrow 2C side in FIG. 2B.
Figure 2D:
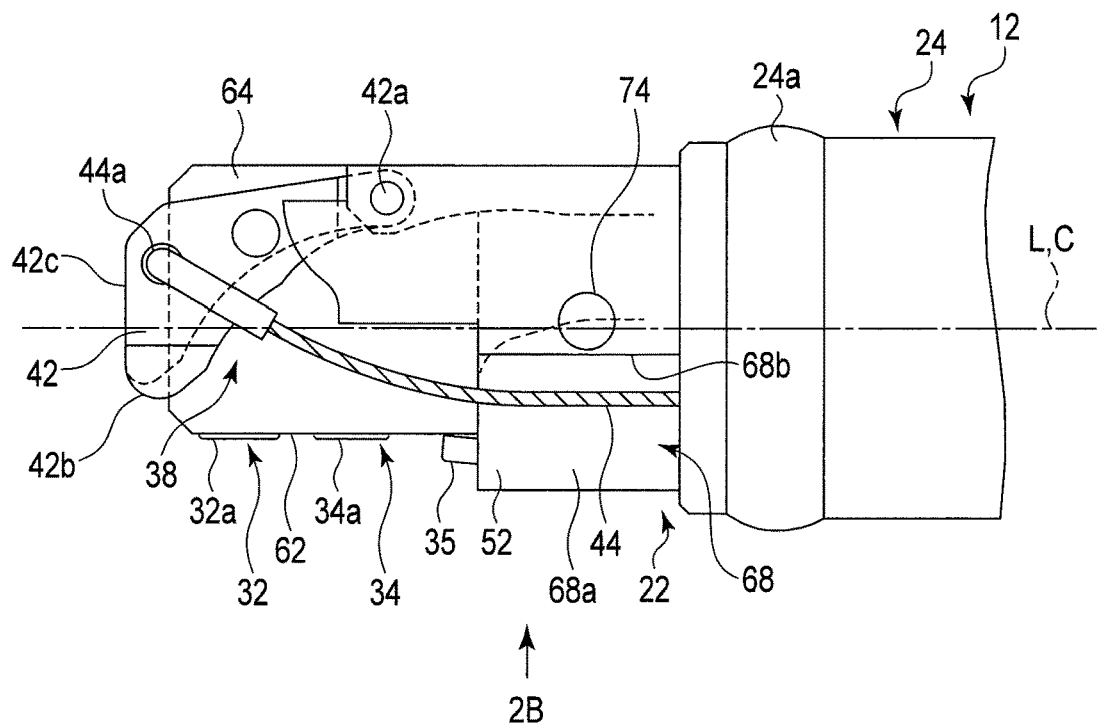
FIG. 2D is a view of the distal framing portion of the endoscope according to the first embodiment viewed from an arrow 2D side in FIG. 2B.

As shown in FIG. 1, an endoscope (insertion device) 10 according to the present embodiment includes an insertion section 12 that is to be inserted into a duct such as a lumen, an endoscope cover (hereinafter mainly referred to as a cover) 14 attached to a distal end of the insertion section 12, an operation section 16 provided at a proximal end of the insertion section 12 and held by a user, and a universal cord 18 extending from the operation section 16. The cover 14 is formed to be disposable, as will be described in detail later. The cover 14 is easily attachable to a distal framing portion 22 of the insertion section 12 with the shape of the cover 14 maintained, but is configured so as not to be easily removed from the distal framing portion 22 unless at least part of the cover 14 is broken.

The insertion section 12 defines a longitudinal axis L by its distal end and proximal end. The insertion section 12 includes, in the order from the distal end to the proximal end, the distal framing portion 22, a bending portion 24, and a tubular portion 26. The tubular portion 26 may be a so-called flexible scope, which has flexibility, or may be a so-called rigid scope, which maintains a straight state and is resistant to bending. The bending portion 24 can be bent in multiple directions such as in two directions including upward and downward directions, or in four directions including upward, downward, rightward, and leftward directions in response to the operation of a knob 16a of the operation section 16, using a publicly known mechanism.

The endoscope 10 is publicly known and therefore will be briefly discussed. The endoscope 10 includes an illumination optical system 32, an observation optical system 34, and a treatment instrument insertion channel 36. Additionally, the endoscope 10 includes an air/water supply mechanism and a suction mechanism that are not shown. The air/water supply mechanism includes a nozzle 35 at its distal end, which is described later, and is operated by a button 17a provided in the operation section 16. The suction mechanism communicates with the treatment instrument insertion channel 36, and is operated by a button 17b provided in the operation section 16.

The illumination optical system 32 and the observation optical system 34 are inserted through the distal framing portion 22, the bending portion 24, and the tubular portion 26 of the insertion section 12, the operation section 16, and the universal cord 18 in the endoscope 10. The illumination optical system 32 has an illumination window 32a in the distal framing portion 22. The observation optical system 34 has an observation window 34a in the distal framing portion 22.

The channel 36 has a distal end that is open into the distal framing portion 22 of the insertion section 12 of the endoscope 10, and has a proximal end that is open in the vicinity of a proximal portion of the tubular portion 26 of the insertion section 12 or into the operation section 16. Here, as shown in FIG. 1, the operation section 16 has an opening (not shown) at the proximal end of the channel 36, and a forceps plug 36b is attachable to and detachable from this opening via a pipe sleeve. The channel 36 has a tube 36a with its distal end fixed to the distal framing portion 22 via a pipe sleeve 36c. Furthermore, the tube 36a of the treatment instrument insertion channel 36 includes a suction path 36d that is publicly known, which is branched therefrom inside the operation section 16, for example. The suction path 36d is coupled to the button 17b, and, when a press operation of the button 17b is performed, a suctioned object is discharged through a later-described opening 66 at the distal end of the channel 36 via the pipe sleeve 36c, the tube 36a, the suction path 36d, and the universal cord 18.

According to the present embodiment, the distal framing portion 22 is formed as a side-viewing type, in which the direction of observation direction differs from the direction along the longitudinal axis L of the insertion section 12. The endoscope 10 includes, at the distal framing portion 22, a swing mechanism 38 for suitably adjusting the orientation of a treatment instrument (not shown) or the like passing through the channel 36 so that the treatment target can be observed in the field of view.

The swing mechanism 38 is publicly known and therefore will be briefly discussed. The swing mechanism 38 has a distal end in the distal framing portion 22 of the insertion section 12 of the endoscope 10, and a proximal end in the operation section 16. The swing mechanism 38 includes a swing table 42, a wire 44, and a lever 46, in the order from the distal end to the proximal end of the insertion section 12.

The swing table 42 is supported on the distal framing portion 22 by a support pin 42a. The distal end of the wire 44 is supported on the swing table 42, and the proximal end of the wire 44 is supported on the lever 46. In addition, a publicly known mechanism is adopted to prevent liquid or gas from penetrating the inside of the insertion section 12, or more specifically, the inside of the tubular portion 26 of the insertion section 12 along the wire 44. Preferably, liquid or gas should be prevented from penetrating the operation section 16 of the insertion section 12 and the tubular portion 26.

As shown in FIGS. 2A to 3B, the distal framing portion 22 includes a block-shaped main body 52. The main body 52 may be a cylindrical component of a rigid material such as stainless steel, which includes a flat portion 62, a storage portion (storage space) 64, an opening 66, a wire moving portion (wire moving region) 68, a guide groove (first guide) 70, and a pin fixing portion 72. The main body 52 defines the central axis C. For the sake of simplicity, it is assumed here that the above-described longitudinal axis L coincides with the center axis C.

The main body 52 is provided with the illumination window 32a at the distal end of an illumination optical system 32, the observation window 34a at the distal end of an observation optical system 34, the pipe sleeve 36c at the distal end of the tube 36a of the channel 36, and the swing table 42 at the distal end of the swing mechanism 38. The distal framing portion 22 is therefore constituted by the main body 52, the illumination window 32a of the illumination optical system 32, the observation window 34a of the observation optical system 34, the pipe sleeve 36c of the distal end portion of the tube 36a of the channel 36, the swing table 42 of the swing mechanism 38, and the wire 44.

Figure 3A:
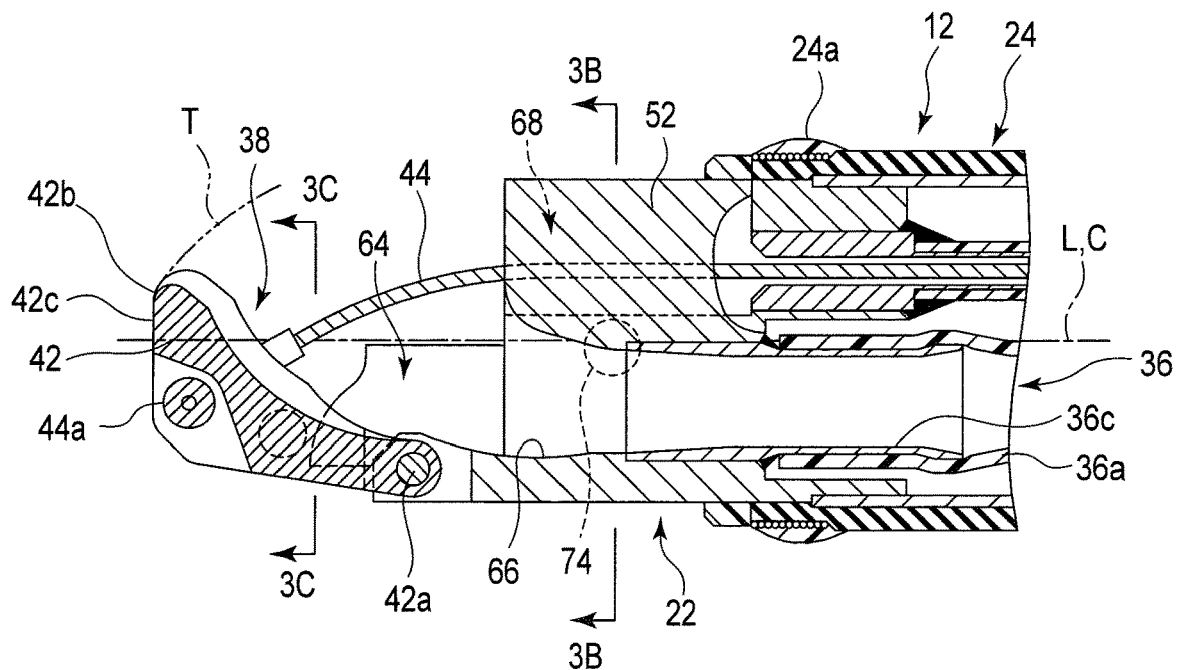
FIG. 3A is a schematic longitudinal sectional view of the distal framing portion of the endoscope according to the first embodiment, taken along the line 3A-3A in FIG. 2B.

The main body 52 includes the flat portion 62 in which the illumination window 32a and the observation window 34a are fixed, a storage portion 64 that swingably accommodates the swing table 42, and the opening 66 that communicates with the storage portion 64 to guide a treatment instrument to the swing table 42. As shown in FIG. 3A, the distal end of the tube 36a of the channel 36 is fixed to the opening 66. It is preferable that the distal end side of the storage portion 64 along the longitudinal axis L, or in other words, the distal end of the main body 52, is open. A wire moving portion 68 is formed on the proximal end side of the storage portion 64 so as to move the wire 44 continuously from the storage portion 64. The wire moving portion 68 is formed on the upper side with respect to the opening 66 in FIG. 3B. The wire moving portion 68 is positioned adjacent to the flat portion 62 in the main body 52, and is formed by walls 68a, 68b and 68c for guiding the wire 44 (see FIG. 2A). It is preferable that the walls 68a, 68b, and 68c of the wire moving portion 68 create a closed space together with a cover main body 102.

The flat portion 62 of the main body 52 is parallel to the longitudinal axis L. For the simplicity of explanation, the flat portion 62 is formed so that a normal line N to the flat portion 62 is directed to a direction substantially orthogonal to the longitudinal axis L. Preferably, the normal line N coincides with the "up" direction of the bending directions of the bending portion 24. When the up direction of the insertion section 12 is defined, and the "down", "right", and "left" directions are determined accordingly. In the flat portion 62 of the main body 52, the illumination window 32a is arranged on the distal side, and the observation window 34a is arranged on the proximal side adjacent to the illumination window 32a. The nozzle 35 is provided on the proximal side of the observation window 34a. The nozzle 35 is directed to the observation window 34a and the illumination window 32a. The nozzle 35 is configured to discharge a liquid such as physiological saline toward the observation window 34a and the illumination window 32a, and also to supply air and water to blow off substances adhered on the observation window 34a and the illumination window 32a.

The storage portion 64 is arranged adjacent to the flat portion 62 in a direction orthogonal to the longitudinal axis L. The storage portion 64 forms a space in which the swing table 42 can turn in a predetermined range. The swing table 42 is swingably supported on the main body 52 by the support pin 42a. When the swing table 42 is disposed at a position shown in FIGS. 2A to 3A (lowered position), a distal face 42c of the swing table 42, including a distal end portion 42b protrudes from the distal end of the main body 52 along the longitudinal axis L.

A distal end 44a of the wire 44 of the swing mechanism 38 is supported by the swing table 42. The proximal end (not shown) of the wire 44 of the swing mechanism 38 is supported by the lever 46 of the operation section 16. By adjusting the length of the wire 44, the swing table 42 is disposed at the position shown in FIGS. 2A to 3A (lowered position) with the lever 46 at a first position (i.e. when the lever 46 is raised to the maximum). As the lever 46 is pushed down, the wire 44 is pulled so that the distal end portion 42b of the swing table 42 that is provided away from the support pin 42a swings along a virtual line T shown in FIG. 3A, with the support pin 42a serving as a pivot. The lever 46 is pushed down to the maximum is brought to a second position. At this position, the swing table 42 is disposed at a raised position where the swing table 42 is raised to the maximum.

As illustrated in FIGS. 2A to 2C, 3B, and 3C, the main body 52 of the distal framing portion 22 includes, on its outer peripheral surface, the guide groove (first restriction portion) 70 as the first guide along the longitudinal axis L. The guide groove 70 is positioned adjacent to the flat portion 62, but is separate from the storage portion 64, or in other words, separate from the wire 44 and the swing table 42 of the swing mechanism 38. It is preferable that the guide groove 70 be continuously formed from the distal end to the proximal end of the main body 52.

The pin fixing portion 72 is formed on the outer peripheral surface of the main body 52 of the distal framing portion 22. It is preferable that the pin fixing portion 72 be formed adjacent to the wire moving portion 68 and on the side substantially opposite to the guide groove 70 across the central axis C of the main body 52 of the distal framing portion 22. A lock pin (lock portion) 74 protruding in the direction orthogonal to the central axis C is fixed to the pin fixing portion 72.

Figure 3B:
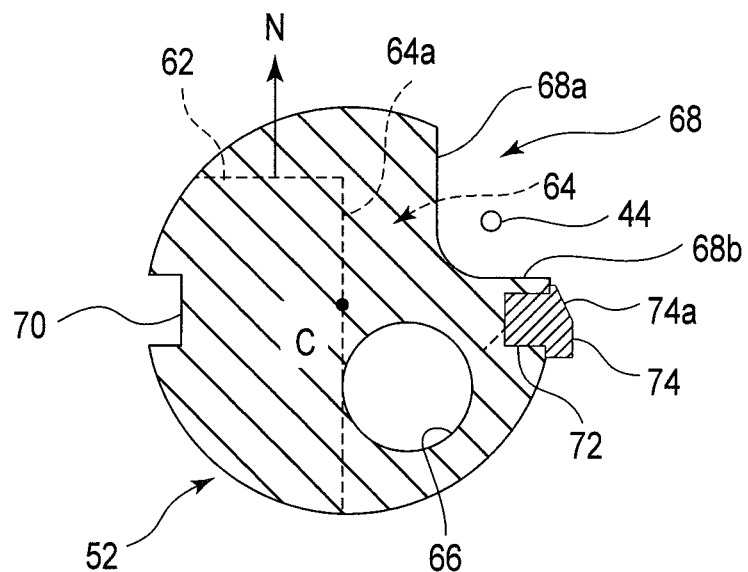
FIG. 3B is a schematic cross sectional view of the distal framing portion of the endoscope according to the first embodiment, taken along the line 3B-3B in FIG. 3A.
Figure 3C:
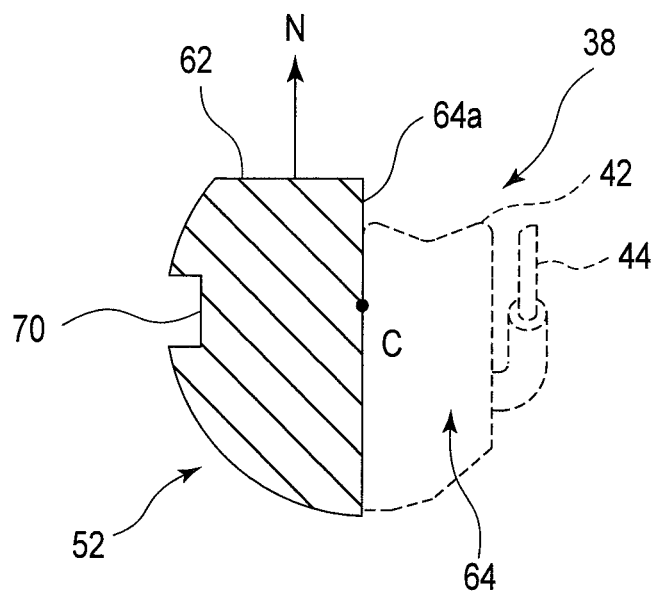
FIG. 3C is a schematic cross sectional view of the distal framing portion of the endoscope according to the first embodiment, taken along the line 3C-3C in FIG. 3A.

With respect to the wall surface 64a of the storage portion 64 shown in FIGS. 3B and 3C as a reference surface, the right side where the swing mechanism 38 is provided is referred to as a first region, and the left side including the flat portion 62 where the illumination optical system 32 and the observation optical system 34 are provided is referred to a second region. The lock pin 74 is positioned in the first region, and the guide groove (first restriction portion) 70 is positioned in the second region, separate from the lock pin 74.

It is preferable that the lock pin 74 shown in FIG. 3B includes an inclined plane 74a. The inclined plane 74a is formed so that the protrusion on the side close to the wire moving portion 68 with respect to the center axis C is small, and the protrusion increases as it is farther from the wire moving portion 68.

Next, the disposable type endoscope cover 14 that is to be attached to the distal framing portion 22 is described with reference to FIGS. 4A to 5D.

Figure 4A:
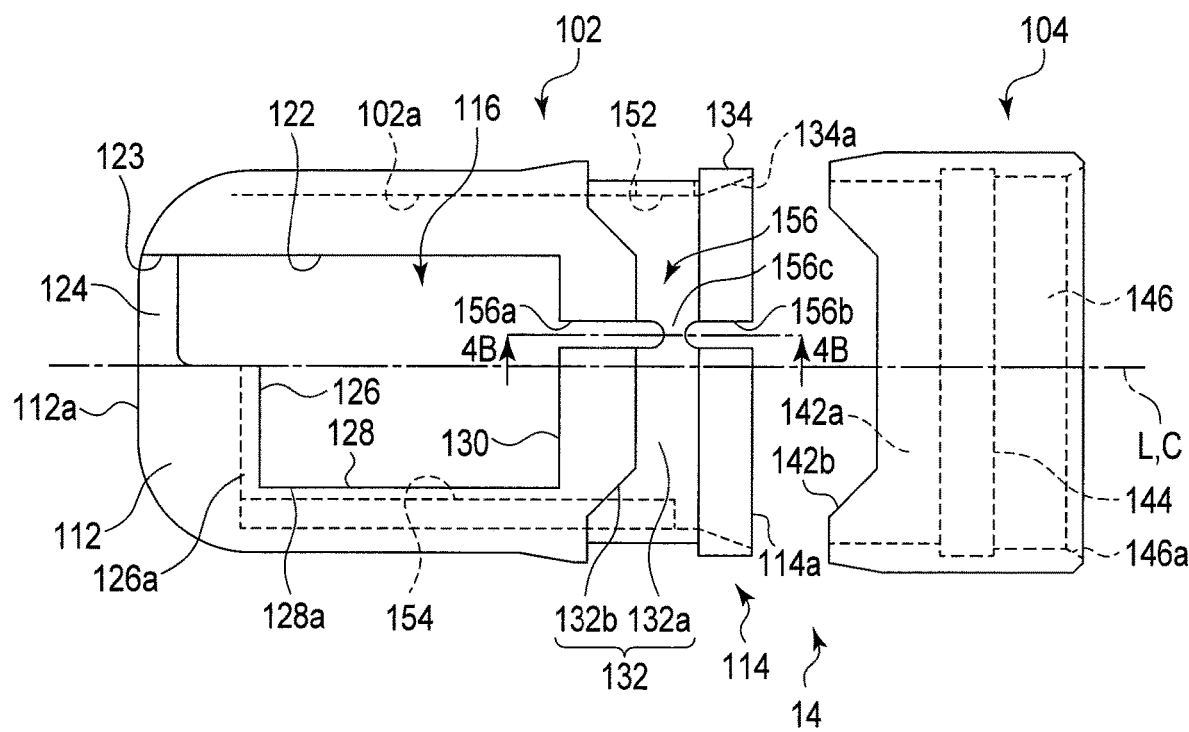
FIG. 4A is a schematic view showing an endoscope cover that is to be attached to the distal framing portion of the endoscope, in a state that the endoscope cover is disassembled, according to the first embodiment.

As shown in FIG. 4A, the endoscope cover 14 according to this embodiment includes the cover main body 102 which is to be attached to the distal framing portion 22 along the longitudinal axis L of the insertion section 12, and a presser ring 104. The cover main body 102 is integrally formed of, for example, a resin material into a cylindrical shape. The presser ring 104 is formed of, for example, a rubber material into a cylindrical shape or an annular shape. The cover main body 102 and the presser ring 104 are preferably made of an electrically insulating material. The inner diameters and inner peripheral surfaces 102a and 104a of the cover main body 102 and the presser ring 104 are formed into suitable sizes and shapes in accordance with the size of the distal framing portion 22.

The cover main body 102 includes a closed portion 112 at its distal end, and an annular portion 114 at its proximal end surrounding the periphery of the distal framing portion 22. The closed portion 112 is formed into a substantially semi-spherical surface. The proximal end of the cover main body 102, or in other words, the proximal end 114a of the annular portion 114, is open.

As shown in FIG. 4A, the cover main body 102 has an open edge 116 having a substantially C-shaped cross section between the closed portion 112 and the annular portion 114. The open edge 116 is open, for example, in the direction orthogonal to the longitudinal axis L. The open edge 116 exposes the illumination window 32a, the observation window 34a, the nozzle 35, and the swing table 42 of the distal framing portion 22 through the open edge 116 to the outside.

Figure 5A:
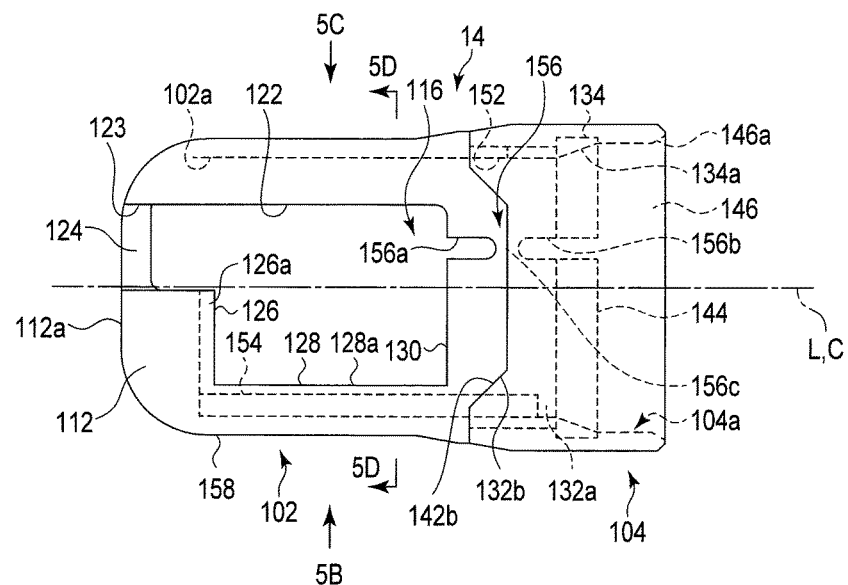
FIG. 5A is a schematic view showing the endoscope cover that is to be attached to the distal framing portion of the endoscope according to the first embodiment.
Figure 5B:
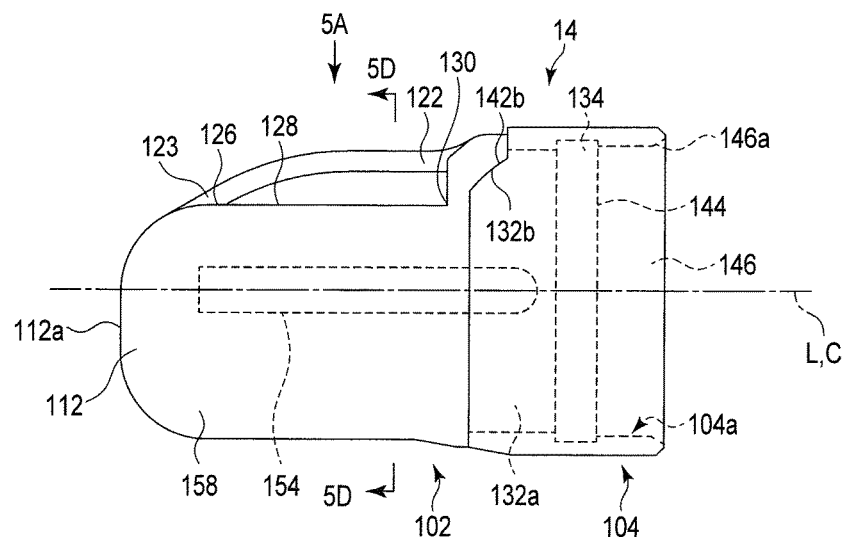
FIG. 5B is a view of the endoscope cover that is to be attached to the distal framing portion of the endoscope according to the first embodiment viewed from an arrow 5B side in FIG. 5A.
Figure 5C:
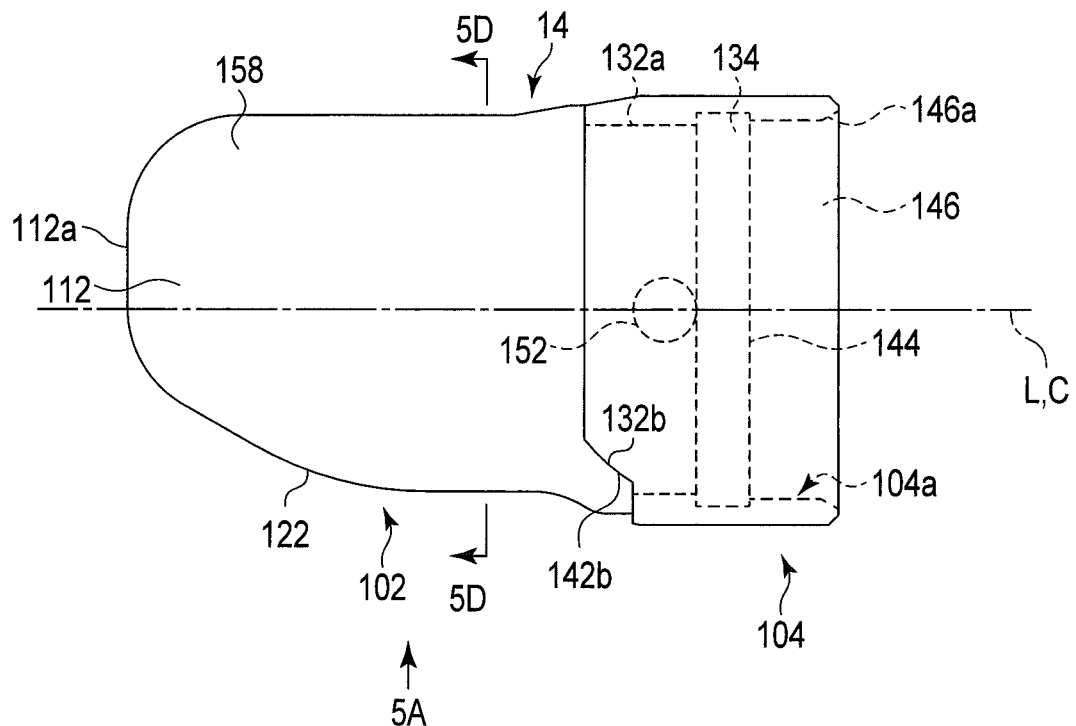
FIG. 5C is a view of the endoscope cover that is to be attached to the distal framing portion of the endoscope according to the first embodiment viewed from an arrow 5C side in FIG. 5A.
Figure 5D:
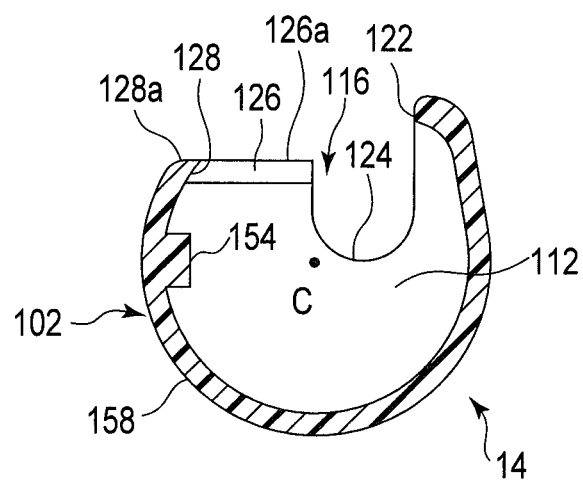
FIG. 5D is a schematic cross sectional view of the endoscope cover that is to be attached to the distal framing portion of the endoscope according to the first embodiment, taken along the line 5D-5D in FIG. 5B.

As shown in FIGS. 5A, 5B, and 5D, the open edge 116 includes a right side edge 122 on the right side of the longitudinal axis L when viewed from the proximal side to the distal side, a U-shaped depressed portion 124 continuous with the right side edge 122, a distal side edge 126 continuous with the depressed portion 124, a left side edge 128 provided on the left side of the longitudinal axis L when viewed from the proximal side to the distal side, and a proximal side edge 130 between the right side edge 122 and the left side edge 128 on the proximal side. The open edge 116 forms a closed ring by the right side edge 122, the depressed portion 124, the distal side edge 126, the left side edge 128, and the proximal side edge 130. It is preferable that the right side edge 122 and the left side edge 128 are parallel, or substantially parallel, to each other, and that the distal side edge 126 and the proximal side edge 130 are parallel, or substantially parallel, to each other.

The right side edge 122 cooperates with the annular portion 114 and a later-described rotation peripheral surface 158 (see FIGS. 5A to 5D) to cover the wire 44 of the swing mechanism 38 in a movable manner. The distal side edge 126 has a distal side covering portion 126a that covers the distal side of the flat portion 62 of the main body 52 with respect to the illumination window 32a. Similarly, the left side edge 128 has a left side covering portion 128a that covers the left side of the flat portion 62 of the main body 52 with respect to the illumination window 32a and the observation window 34a.

The U-shaped depressed portion 124 is formed at the distal end of the right side edge 122 continuously with the right side edge 122. The depressed portion 124 is formed toward a distal end 112a of the closed portion 112. As shown in FIGS. 5B and 5C, the portion in which the depressed portion 124 is formed is tapered toward the distal side along the longitudinal axis L.

As shown in FIG. 4A, the annular portion 114 includes, on its outer peripheral surface, an attachment portion 132 to which the presser ring 104 is fitted. The attachment portion 132 is formed circumferentially on the proximal side of the proximal side edge 130 of the open edge 116 along the longitudinal axis L, at a position away from the proximal side edge 130. The attachment portion 132 includes an annular depressed portion 132a that prevents the presser ring 104 from moving along the longitudinal axis L with respect to the cover main body 102, and an attachment depressed portion 132b that prevents the presser ring 104 from moving around the longitudinal axis L. The annular depressed portion 132a and the attachment depressed portion 132b are formed integrally and continuously with each other. The annular portion 114 has an annular flange portion 134 that is formed on the proximal end side of the attachment portion 132 to protrude from the annular depressed portion 132a outwardly in a radial direction of the longitudinal axis L. Formed on the inner periphery of the flange portion 134 is a skirt portion 134a, which is configured to be thinner toward the proximal side along the longitudinal axis L. The inner diameter of the skirt portion 134a increases toward the proximal side. It is preferable that the skirt portion 134a is tapered.

It is preferable that the inner diameter of the inner peripheral surface 102a of the cover main body 102 stay constant from the vicinity of the distal ends of the right side edge 122 and the left side edge 128 of the open edge 116 to the distal end of the skirt portion 134a of the flange portion 134.

The presser ring 104 includes an annular protruding portion 142a formed in the inner peripheral surface 104a of the presser ring 104 to be engaged with the annular depressed portion 132a, and an attachment protruding portion 142b which is to be fitted to the attachment depressed portion 132b. The presser ring 104 includes an annular attachment depressed portion 144 formed in the inner peripheral surface 104a of the presser ring 104, to which the flange portion 134 is to be engaged with the proximal side of the annular protruding portion 142a. In this manner, the presser ring 104 is engaged with the annular portion 114 of the cover main body 102, as shown in FIGS. 5A to 5C and 6. The presser ring 104 includes an attachment portion 146 formed on the inner peripheral surface 104a on the proximal side of the attachment depressed portion 144 to be fitted to the thread wound portion 24a at the distal end portion of the bending portion 24. A skirt portion 146a that is configured to be thinner toward the proximal side along the longitudinal axis L is formed on the inner periphery of the proximal end of the attachment portion 146. The inner diameter of the skirt portion 146a increases toward the proximal side. The skirt portion 146a is preferably tapered.

As shown in FIGS. 4A, 5A, 5C, and 6, a lock depressed portion (lock portion) 152 is formed in the inner peripheral surface 102a of the annular portion 114 at the proximal end of the cover main body 102 to be engaged with the lock pin 74. That is, the lock depressed portion (lock portion) 152 engages the cover main body 102 with the distal framing portion 22. The lock depressed portion 152 may be formed in a manner that the inner peripheral surface 102a of the cover main body 102 communicates with the outer peripheral surface, or may be formed simply to be depressed in the inner peripheral surface 102a of the cover main body 102. It is preferable that the lock depressed portion 152 is formed in the annular depressed portion 132a.

A guide protruding portion (second guide) 154 is formed in the inner peripheral surface 102a of the cover main body 102 to be movable along the guide groove 70. That is, the guide protruding portion 154 protrudes inwardly from the inner peripheral surface 102a of the cover main body 102 in the radial direction. It is preferable that the guide protruding portion 154 is formed to extend from the vicinity of the distal end to the vicinity of the proximal end of the inner peripheral surface 102a of the cover main body 102. The guide protruding portion 154 may be formed into a suitable shape, and may be formed to have substantially a rectangular cross section, as shown in FIG. 5D. Otherwise, although not shown, more than one guide protruding portion 154 may be formed and spaced apart at suitable intervals.

Figure 4B:
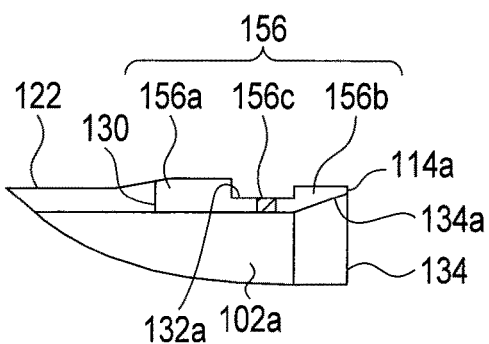
FIG. 4B is a schematic longitudinal sectional view of the endoscope cover that is to be attached to the distal framing portion of the endoscope according to the first embodiment, taken along the line 4B-4B in FIG. 4A.

As shown in FIGS. 4A and 4B, a fragile portion 156 is formed between the proximal side edge 130 of the open edge 116 of the cover main body 102 and the proximal end 114a of the flange portion 134 of the annular portion 114. The fragile portion 156 has a portion that is fragile, for which the mechanical strength against breakage under an externally applied stress is determined to be lower than the rest of adjacent portions. The fragile portion 156 is to be broken when the cover 14 is removed from the distal framing portion 22. At least part of the fragile portion 156 is therefore positioned in the annular portion 114 of the cover main body 102. The fragile portion is configured so that the annular portion 114 can be broken when intended stress is applied to the annular portion 114. The fragile portion 156 is lower in mechanical strength than the rest of the annular portion 114. Here, the fragile portion 156 has slits 156a and 156b. One slit 156a is formed continuously with the proximal side edge 130 of the open edge 116. The other slit 156b is formed continuously with the proximal end 114a of the flange portion 134 of the annular portion 114. The slits 156a and 156b are formed along the longitudinal axis L. The slits 156a and 156b are not communicated with each other, and a coupling portion 156c is formed between the slits 156a and 156b. Thus, the annular depressed portion 132a of the annular portion 114 is formed to be annular. The lock depressed portion 152 is formed at a position approximately 90° away from the coupling portion 156c in the peripheral direction with respect to the longitudinal axis L. The guide protruding portion 154 is formed at a position approximately 90° away from the coupling portion 156c on the side opposite to the lock depressed portion 152 in the peripheral direction of the longitudinal axis L. It is preferable that the fragile portion 156 is positioned approximately 90° away from each of the guide protruding portion 154 and the lock depressed portion 152 in the peripheral direction of the central axis C. That is, the position of the guide protruding portion 154 differs from the position of the lock depressed portion 152 in the peripheral direction with respect to the longitudinal axis L. It is further preferable that, as described later, the fragile portion 156 is positioned more than 90° away from the guide protruding portion 154 in the peripheral direction, and that the distance between the fragile portion 156 and the lock depressed portion 152 be shorter than the distance between the guide protruding portion 154 and the fragile portion 156.

The fragile portion 156 includes the slits 156a and 156b, and therefore a portion that has a thickness to form the annular portion 114 is provided only in the coupling portion 156c. With such a structure, when stress is externally applied to the annular portion 114, the stress is concentrated on the coupling portion 156c. Thus, the coupling portion 156c is easily and mechanically broken in comparison with the rest of the annular portion 114. In other words, the fragile portion 156 that is the entire fragile portion including the slits 156a and 156*b* and the coupling portion 156*c*, has a mechanical strength lower than the rest of the annular portion 114.

According to the present embodiment, the fragile portion 156 is preferably formed not in the flat portion 62 of the main body 52 of the distal framing portion 22, but above the wire moving portion (wire moving space) 68. The slit 156*b* on the proximal side contributes to the elastic deformation of the annular portion 114. That is, the flange portion 134 is elastically deformed when the lock depressed portion 152 is engaged with the lock pin 74.

As shown in FIGS. 5A to 5D, the cover main body 102 has, in its outer periphery, the rotation peripheral surface 158. The rotation peripheral surface 158 is formed as part of the circular cylinder. The central axis C of the cover 14 and the distal framing portion 22 is defined by the rotation peripheral surface 158. The rotation peripheral surface 158 is fitted to a support peripheral surface 214 of a jig 200, which will be described later.

When the cover 14 is prepared, the presser ring 104 is attached to the cover main body 102 shown in FIG. 4A. First, the user checks to confirm that the coupling portion 156*c* is present between the slits 156*a* and 156*b* of the cover main body 102, and that the slits 156*a* and 156*b* are not continuous with each other. Then, as shown in FIGS. 5A to 5C, the presser ring 104 is fitted to the cover main body 102 to obtain the cover 14.

As shown in FIG. 6, the cover 14 is attached to the distal framing portion 22 by aligning the cover 14 with the distal framing portion 22 in the peripheral direction with respect to the longitudinal axis L. The guide protruding portion 154 of the cover 14 is engaged with the guide groove 70 of the main body 52 of the distal framing portion 22, and the cover 14 is moved along the longitudinal axis L. This prevents the cover 14 from being displaced with respect to the distal framing portion 22 in the peripheral direction.

When the cover 14 is attached to the distal framing portion 22, the skirt portion 146*a* of the attachment portion 146 of the presser ring 104 of the cover 14 is in contact with the lock pin 74 of the distal framing portion 22. At this point, the attachment portion 146, which has elasticity, is elastically deformed to move on the lock pin 74. The lock pin 74 of the distal framing portion 22 is therefore brought into contact with the skirt portion 134*a* of the annular portion 114 of the cover main body 102. At this point, the annular portion 114 is elastically deformed by the slit 156*b*. As a result, the lock depressed portion 152 engages with the lock pin 74 of the distal framing portion 22. Then, the displacement of the cover 14 with respect to the distal framing portion 22 in the axial direction and in the peripheral direction can be prevented.

Figure 7:
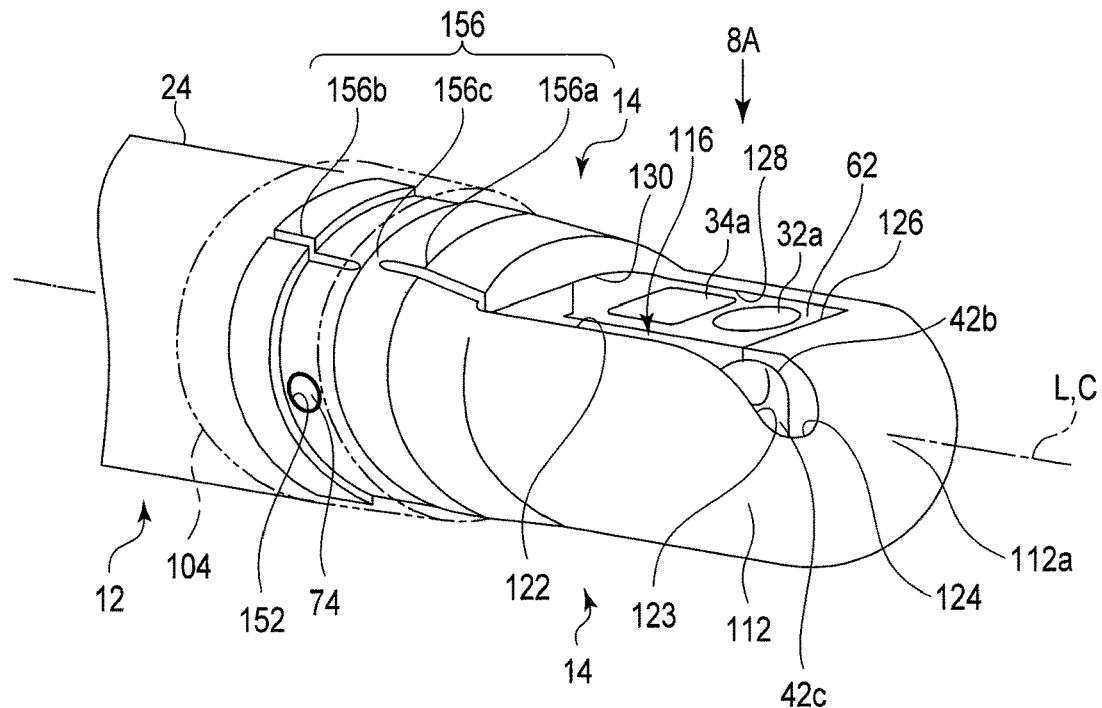
FIG. 7 is a schematic perspective view showing the endoscope cover in a state of having been attached to the distal framing portion of the endoscope according to the first embodiment.
Figure 8A:
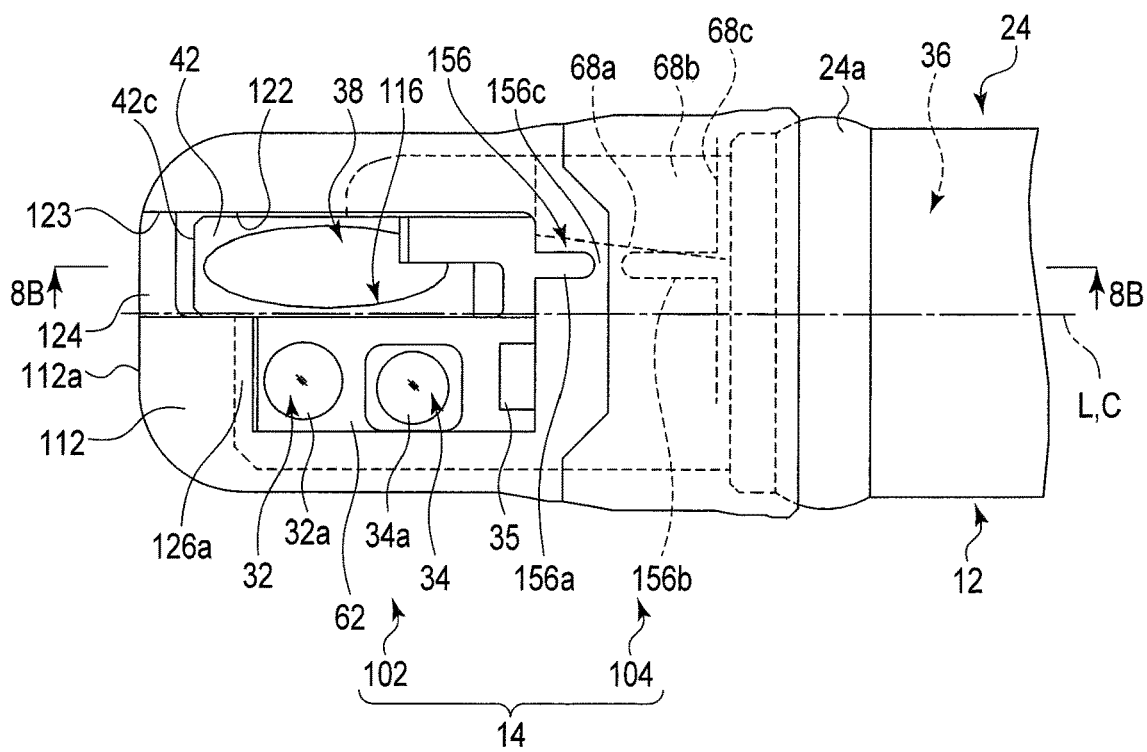
FIG. 8A is the endoscope cover in a state of having been attached to the distal framing portion of the endoscope according to the first embodiment as viewed from an arrow 8A side in FIG. 7.
Figure 8B:
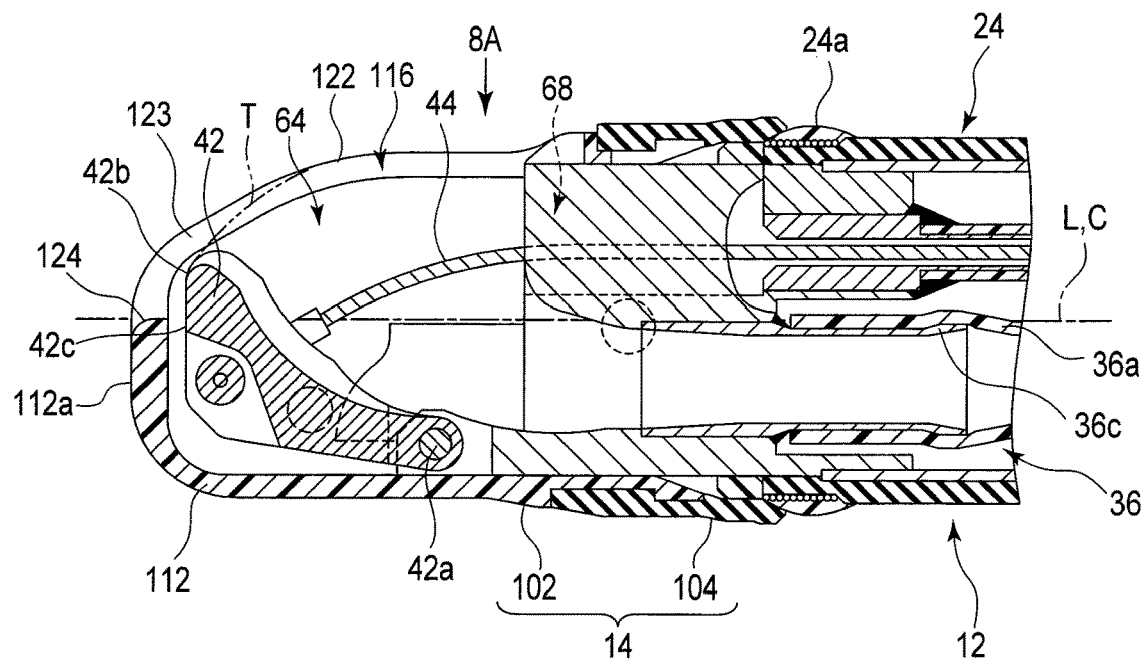
FIG. 8B is a schematic longitudinal sectional view of the endoscope cover that has been attached to the distal framing portion of the endoscope according to the first embodiment, taken along the line 8B-8B in FIG. 8A.

As shown in FIGS. 7 to 8B, the skirt portion 146*a* of the attachment portion 146 of the presser ring 104 of FIGS. 5A to 5C may be in contact with the thread wound portion 24*a* at the distal end of the bending portion 24. The thread wound portion 24*a* is prepared by annularly winding a thread and applying an adhesive to the outer periphery of the wound thread to provide a portion in which the applied adhesive is fixed.

Figure 9:
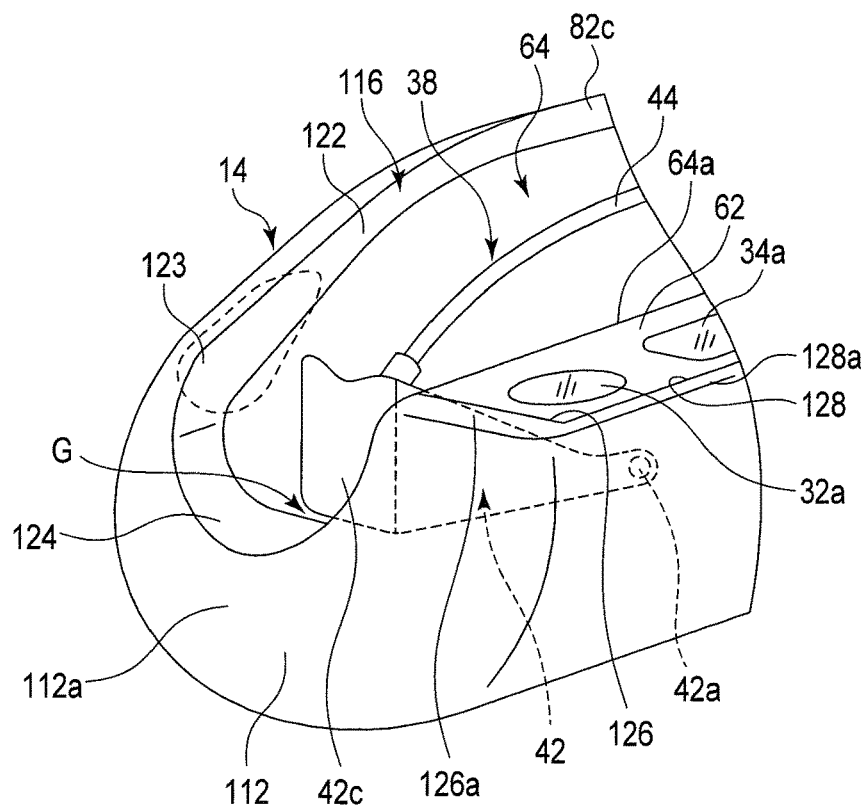
FIG. 9 is a schematic perspective view showing the vicinity of a distal portion in a state in which the endoscope cover has been attached to the distal framing portion of the endoscope according to the first embodiment.

As shown in FIGS. 7 to 9, the illumination window 32*a*, the observation window 34*a*, and the nozzle 35 are exposed from the open edge 116 of the cover 14, and the swing table 42 is exposed to be swingable in a suitable range. With the cover 14 suitably attached to the distal framing portion 22, the distal end portion 42*b* and part of the distal face 42*c* of the swing table 42 are exposed when viewed from the distal side of the longitudinal axis L. Thus, when a not-shown treatment instrument is guided by the swing table 42 to protrude from the distal end of the swing table 42, the depressed portion 124 can prevent the treatment instrument from interfering with the cover 14. In addition, in order to suppress friction between the swing table 42 and the cover main body 102 that is attached to the distal framing portion 22, a gap G is provided between the swing table 42 and the cover main body 102. In particular, the gap G is formed between the distal face 42*c* of the swing table 42 and the depressed portion 124 of the cover 14. When the swing table 42 is swung, the volume of gap may change between the distal face 42*c* of the swing table 42 and the depressed portion 124 of the cover 14, but the gap is still maintained. The cover main body 102 will therefore be prevent from interfering with the motion of the swing table 42. In the cross section of the distal framing portion 22 to which the cover 14 is attached, the outer peripheral surface as indicated with a reference number 158 forms a partial ring shape.

When the cover 14 attached to the distal framing portion 22 is viewed in a section perpendicular to the longitudinal axis L and then the section is divided into the first region and the second region different from each other as defined above, the lock depressed portion 152 is located in the first region, and the guide protruding portion 154 is located in the second region.

Observation and treatment by inserting the insertion section 12 of the endoscope 10 into a duct such as a lumen is performed when the cover 14 is attached to the distal framing portion 22. It should be noted that the fragile portion 156 is covered and protected by the presser ring 104. For this reason, even if the fragile portion 156 hits the interior wall or the like during the insertion into a duct in a body cavity or the like, or during a treatment, the breakage of the fragile portion 156 can be avoided.

After the use of the endoscope 10, the cover 14 is removed from the distal framing portion 22. The cover main body 102 and the presser ring 104 of the cover 14 are disposed of as-is. The distal framing portion 22, from which the cover 14 is removed, is washed, disinfected, and sterilized to be reused. In other words, the endoscope 10, from which the cover 14 is removed, is washed, disinfected, and sterilized to be reused. Because the cover 14 is removed from the distal framing portion 22, washing can be readily conducted, not only for the vicinity of the illumination window 32*a* of the illumination optical system 32 and the vicinity of the observation window 34*a* of the observation optical system 34, but also for the channel 36 and the swing mechanism 38.

When the cover 14 is removed from the distal framing portion 22, the user breaks the coupling portion 156*c* between the slits 156*a* and 156*b*, using the force of his/her finger, and then the user releases the engagement of the lock depressed portion 152 with the lock pin 74 of the distal framing portion 22. It may be possible to remove the cover 14 by moving it toward the distal side with respect to the central axis C after turning the cover 14 with respect to the distal framing portion 22 around the central axis C to disengage the lock depressed portion 152 from the lock pin 74. However, when removing the cover 14 from the distal framing portion 22 by the user's fingers, the manner of removal may differ depending on the user. They may make it difficult to stably perform the breakage of the fragile portion 156.

The fragile portion 156 may be reliably broken by use of the jig (removal tool for the cover 14) 200 (see FIGS. 10 to 13B) described below. It is therefore preferable that the jig 200 is used when the cover 14 is to be removed from the distal framing portion 22 after the use of the endoscope 10.

The jig 200 is also used for the purpose of reliably breaking the cover 14 and preventing the reuse of the cover 14.

Figure 10:
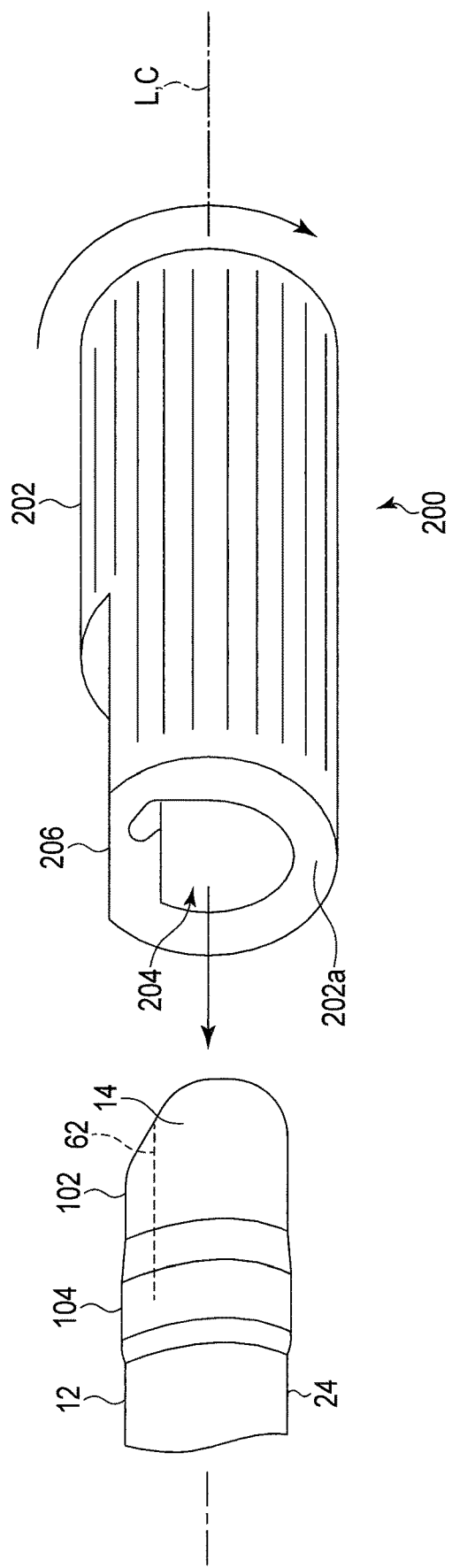
FIG. 10 is a schematic perspective view showing a state in which the endoscope cover according to the first to third embodiments is being removed from the distal framing portion of the endoscope by use of a jig.
Figure 11A:
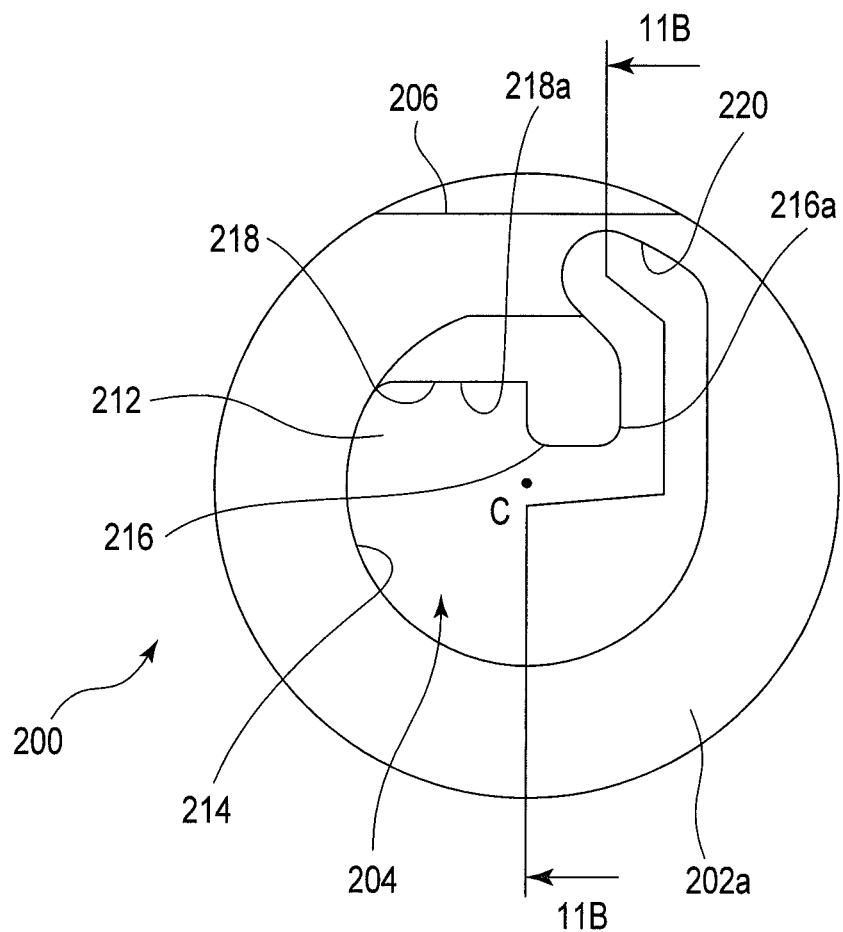
FIG. 11A is a schematic front view showing an acting portion at one end of the jig for removing the endoscope cover from the distal framing portion of the endoscope according to the first to third embodiments.
Figure 11B:
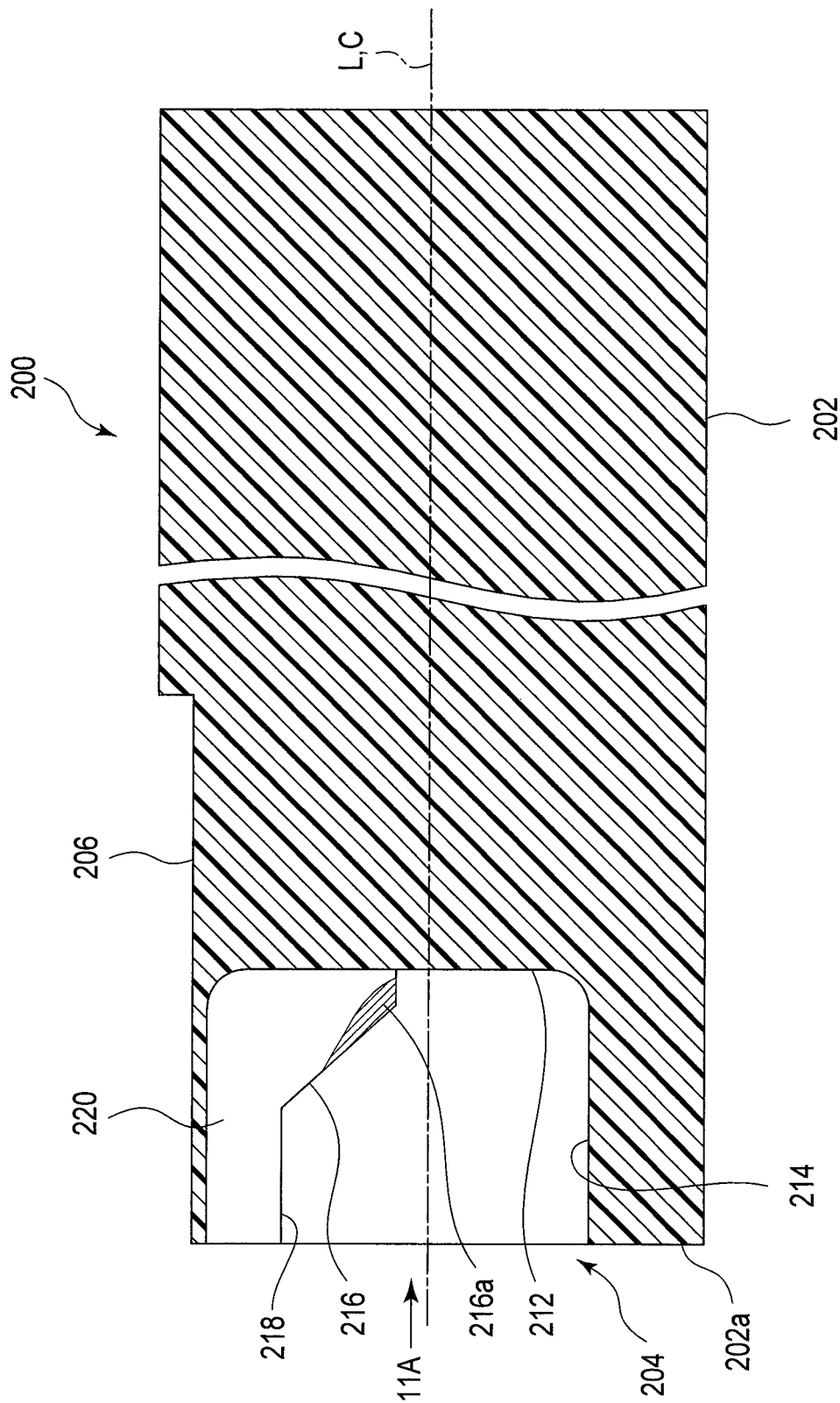
FIG. 11B is a schematic longitudinal sectional view of the acting portion at one end of the jig for removing the endoscope cover from the distal framing portion of the endoscope according to the first to third embodiments, taken along the line 11B-11B in FIG. 11A.

The cover removal jig 200 according to the present embodiment is made of a rigid material such as a resin material that is more rigid than the cover main body 102 of the cover 14, or made of a metallic material. As shown in FIG. 10, the jig 200 includes a column 202. An outer periphery of the column 202 is formed into a suitable shape. As shown in FIGS. 11A and 11B, an acting portion 204, which acts on the cover 14 when removing the cover 14 attached to the distal framing portion 22, is formed at one end 202a of the column 202. The acting portion 204 is shaped into a depression which covers the vicinity of the distal end 112a of the closed portion 112 of the cover 14. An index 206, which allows the user to recognize the direction of the jig 200 in the peripheral direction around the longitudinal axis L, is formed on the outer peripheral surface of the column 202. Here, the index 206 is formed into a plane such that the direction can be recognized when the index 206 is touched. It is preferable that the index 206 is formed at a position adjacent to the acting portion 204.

The index 206 allows the user to visually check and recognize, for example, the position to insert the distal framing portion 22 to which the endoscope cover 14 is attached. The index may be letters such as "up", or may be an arrow imprinted to indicate the rotation direction. The outer shape of the cover removal jig 200 is not specifically limited.

As shown in FIGS. 11A and 11B, the acting portion 204 has a bottom surface 212, a support peripheral surface 214 that is preferably orthogonal to the bottom surface 212, a first protruding portion 216 that is fitted to the U-shaped depressed portion 124 of the open edge 116 of the cover 14, a second protruding portion 218 that is fitted to the distal side covering portion 126a of the cover 14, and a retraction portion 220 into which part of the right side edge 122 of the open edge 116 of the broken cover 14 is retracted.

Figure 12A:
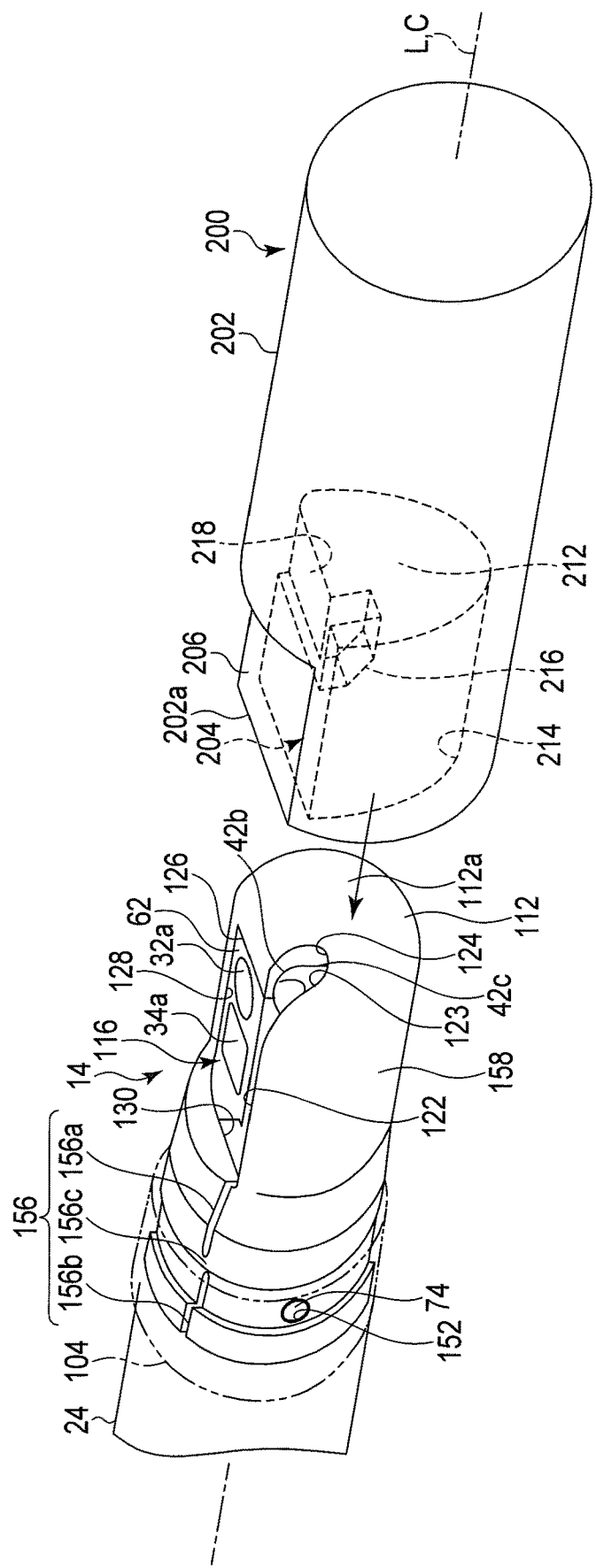
FIG. 12A is a schematic perspective view showing a state in which the jig is being engaged with the endoscope cover to remove the cover from the distal framing portion of the endoscope according to the first embodiment.

As shown in FIGS. 12A and 12B, the acting portion 204 at the one end 202a of the column 202 of the jig 200 is fitted to the distal framing portion 22 with the endoscope cover 14 attached.

As shown in FIG. 13A, the distal end 112a of the closed portion 112 of the cover 14 is brought into contact with the bottom surface 212. Thus, the bottom surface 212 regulates the length of the cover 14 to be inserted in the depressed acting portion 204 from the one end 202a of the jig 200 to be a certain length.

Figure 13B:
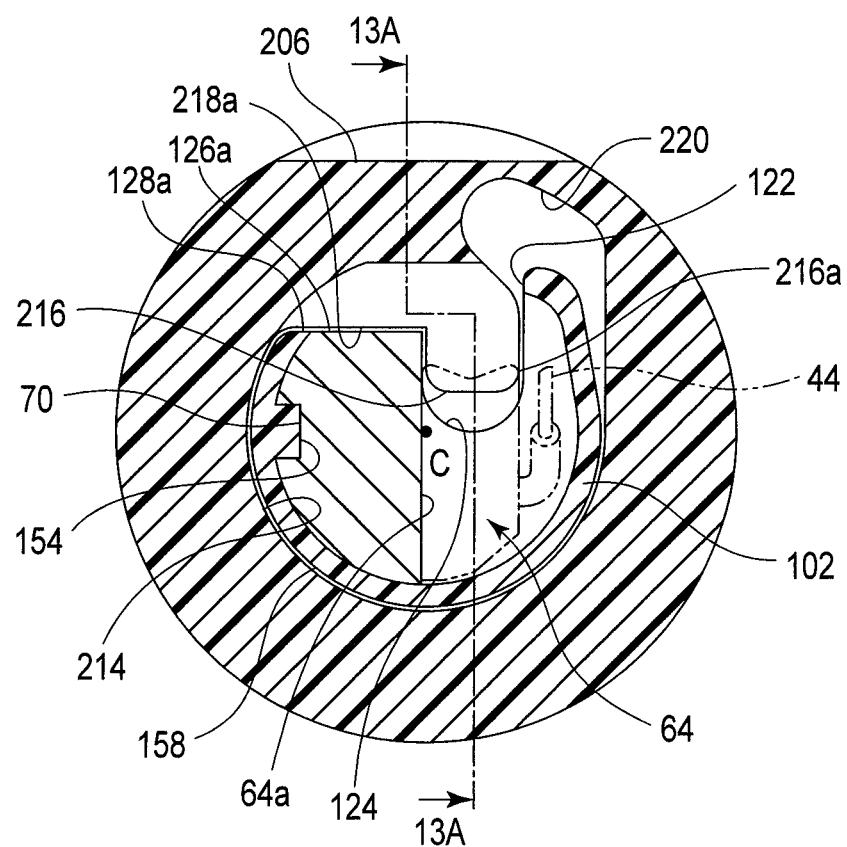
FIG. 13B is a schematic cross sectional view taken along the line 13B-13B in FIG. 13A.

As shown in FIGS. 13A and 13B, the support peripheral surface 214 is formed as a part of the circular form. The central axis C of the acting portion 204 is defined by the support peripheral surface 214. The distance between the central axis C and the support peripheral surface 214, or in other words, the radius of the acting portion 204 is formed to be slightly larger than the radius defined by the rotation peripheral surface 158, which forms a part of the circular cylinder of the cover 14. The rotation peripheral surface 158 of the cover 14 therefore abuts on and is thus supported by, the support peripheral surface 214. At this point, the support peripheral surface 214 is movable relative to the rotation peripheral surface 158 around the central axis C.

As shown in FIGS. 11A and 13A, the first protruding portion 216 protrudes from the bottom surface 212 toward the one end 202a of the column 202. The amount of protrusion of the first protruding portion 216 from the bottom surface 212 is adjusted so that, when the distal end 112a of the closed portion 112 of the cover 14 is brought in contact with the bottom surface 212, the first protruding portion 216 is able to be brought into contact with the depressed portion 124 of the cover 14 and is positioned separate from the distal end portion 42b and the distal face 42c of the swing table 42. Even if the swing table 42 is swung with the distal end 112a of the closed portion 112 of the cover 14 being in contact with the bottom surface 212, the first protruding portion 216 will not be brought into contact with the distal end portion 42b and the distal face 42c of the swing table 42. Moreover, the width of the first protruding portion 216 is determined to be slightly smaller than the width of the depressed portion 124 of the cover 14. The first protruding portion 216 of the jig 200 is provided with a pressure portion 216a which is brought into contact with the pressure receiving portion 123 (see FIG. 9) provided between the depressed portion 124 and the right side edge 122 of the open edge 116 of the cover 14 when the jig 200 is turned with respect to the cover 14 in the peripheral direction of the central axis C.

The second protruding portion 218 shown in FIG. 11A protrudes toward the one end 202a of the column 202 from the bottom surface 212. The second protruding portion 218 is adjacent to the first protruding portion 216 in the peripheral direction of the central axis C. The second protruding portion 218 has an opposed surface 218a, which is preferably parallel to the distal side covering portion 126a. The opposed surface 218a may be in contact with the distal side covering portion 126a of the distal side edge 126 of the cover 14. The opposed surface 218a therefore may indirectly hold the flat portion 62 of the main body 52 of the distal framing portion 22.

The use of the jig 200 for removing the cover 14 attached to the distal framing portion 22 will be explained below.

As shown in FIGS. 10 and 12A, the acting portion 204 of the jig 200 is opposed to the distal framing portion 22 with the cover 14 attached. The orientation of the index 206 is determined to be parallel to the flat portion 62 of the distal framing portion 22. In this state, the acting portion 204 of the jig 200 is fitted onto the cover 14, as shown in FIG. 12B. The central axis C of the support peripheral surface 214 of the jig 200 should be aligned with the central axis C of the rotation peripheral surface 158 of the cover 14, and the distal end 112a of the closed portion 112 of the cover 14 should be brought into contact with the bottom surface 212 of the acting portion 204 of the jig 200.

At this point, the first protruding portion 216 of the jig 200 is fitted into the depressed portion 124 of the open edge 116 of the cover 14, as shown in FIGS. 13A and 13B. The second protruding portion 218 of the jig 200 is brought close to, or in contact with, the distal side covering portion 126a of the cover 14. The second protruding portion 218 supports the position close to the distal side edge 126 between the distal side edge 126 and the distal end 112a of the closed portion 112.

A gap X is created between the first protruding portion 216 and the swing table 42 (i.e., there is a distance X between the first protruding portion 216 and the distal end portion 42b of the swing table 42 in FIGS. 11A to 12A), no matter where the swing table 42 is positioned by swinging. That is, the gap X is greater than 0. For this reason, the swing table 42 would not be brought into contact with the jig 200, wherever the distal end portion 42b is positioned within a swingable range indicated by a virtual line T.

The jig 200 is turned with respect to the distal framing portion 22 and the cover 14 in a direction indicated by an arrow R in FIG. 12B, with the distal framing portion 22 or the vicinity of the distal portion of the insertion section 12 being held and the distal end 112a of the closed portion 112 of the cover 14 being in contact with the bottom surface 212 of the jig 200. In other words, the support peripheral surface 214 of the jig 200 that shares the central axis C with the rotation peripheral surface 158 of the cover 14 is turned around the central axis C.

Figure 13C:
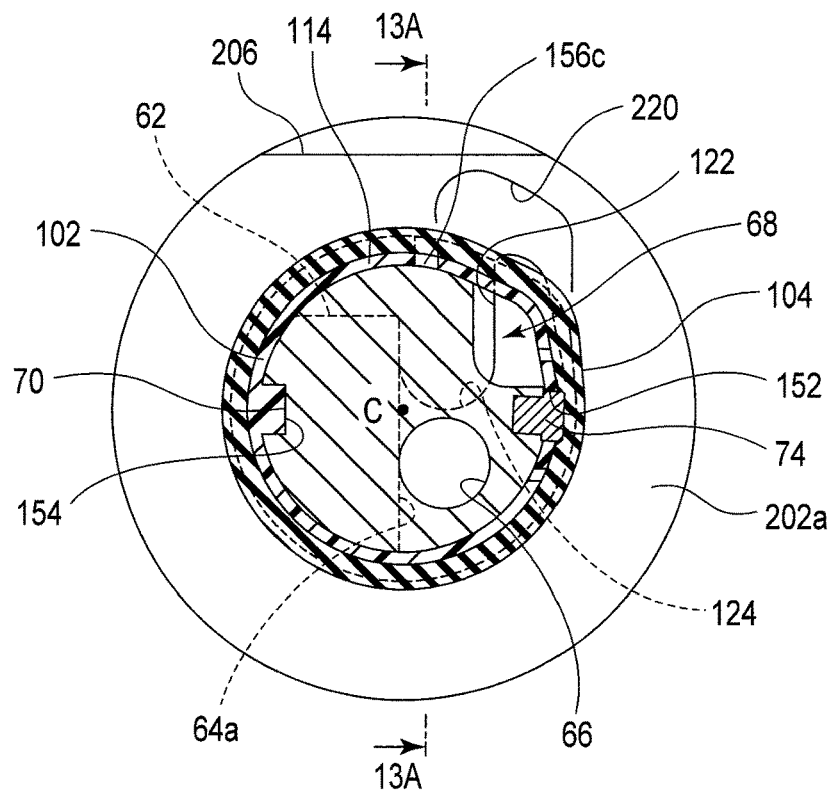
FIG. 13C is a schematic cross sectional view taken along the line 13C-13C in FIG. 13A.
Figure 13D:
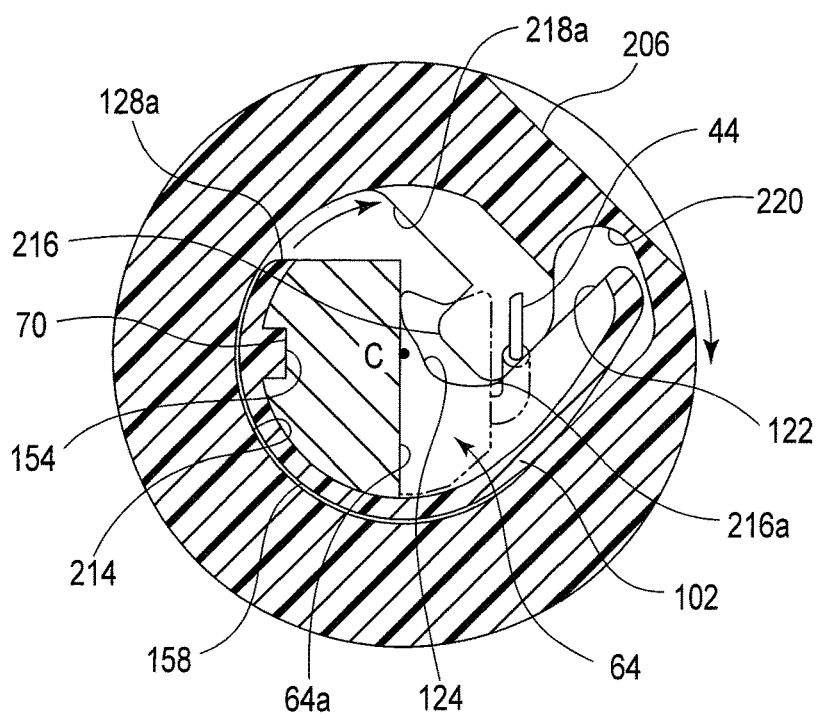
FIG. 13D is a schematic cross sectional view showing the jig engaged with the cover, in a state in which a depressed portion is spread open by pressing the right side edge of an opening edge and turning the jig with respect to the cover from the state shown in FIG. 13B.

As shown in FIGS. 13B and 13D, the pressure receiving portion 123 provided between the right side edge 122 and the depressed portion 124 of the open edge 116 is being pressed by the pressure portion 216a of the first protruding portion 216, while the opposed surface 218a of the second protruding portion 218 of the jig 200 is being moved away from the distal side covering portion 126a of the cover 14.

Here, when the force is applied to the cover main body 102 around the central axis C with the cover main body 102 attached to the distal framing portion 22, the bearing force of the guide protruding portion (second restriction portion) 154 of the cover 14 is determined so that the bearing force is greater than the total of the amount of force that would break the fragile portion 156 and the amount of force that would release the engagement of the lock depressed portion 152 with the lock pin 74. In other words, the guide protruding portion 154 of the cover 14 tries to maintain the engagement with the guide groove 70 of the distal framing portion 22. Thus, the guide protruding portion (second retention portion) 154 regulates the movement of the cover main body 102 with respect to the distal framing portion 22 around the central axis C.

Figure 13E:
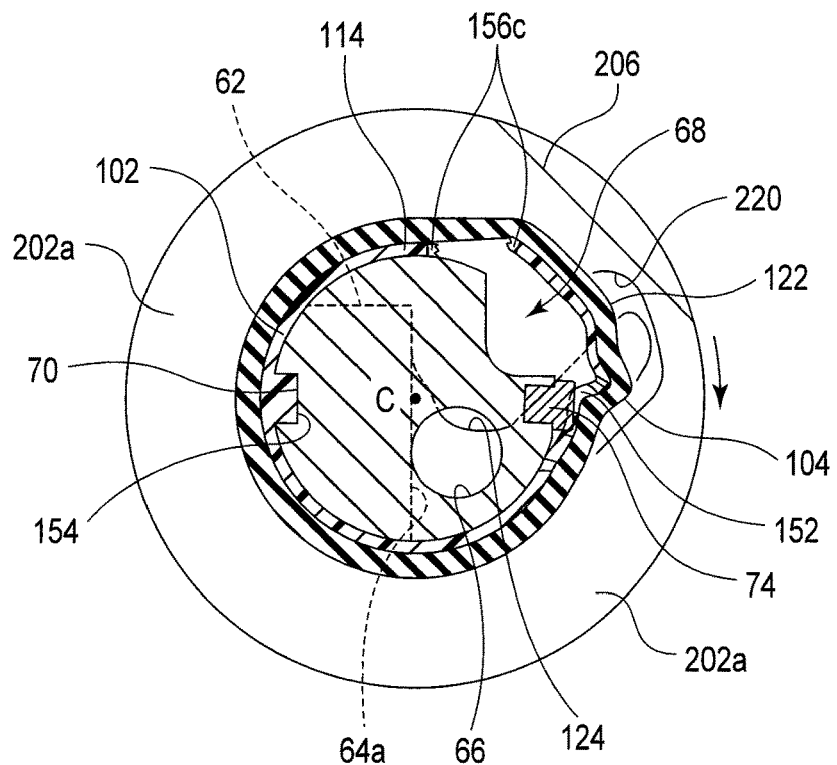
FIG. 13E is a schematic cross sectional view showing the jig engaged with the cover, in a state in which a depressed portion is spread open by pressing the right side edge of an opening edge and turning the jig with respect to the cover from the state shown in FIG. 13C and in which a coupling portion of a fragile portion is thereby broken.

As shown in FIGS. 13C and 13E, the operation force of the jig 200 is applied to the coupling portion 156c between the slits 156a and 156b of the cover 14 facing the first protruding portion 216 of the jig 200 via the pressure receiving portion 123, the right side edge 122, and the proximal side edge 130, as a result of which the coupling portion 156c is broken. Due to the breakage of the coupling portion 156c, part of the attachment portion 132 of the annular portion 114 including the lock depressed portion 152 moves in the peripheral direction, while the engagement of the guide protruding portion 154 of the cover 14 with the guide groove 70 of the distal framing portion 22 is maintained. In conjunction with the breakage of the coupling portion 156c, the engagement of the lock depressed portion 152 with the lock pin 74 is released.

The inclined plane 74a of the lock pin 74 is provided on the side close to the coupling portion 156c. With the structure having such an inclined plane 74a, the lock depressed portion 152 slips along the inclined plane 74a with the momentum of the coupling portion 156c that is being broken. The engagement of the lock depressed portion 152 with the lock pin 74 therefore can be easily released with the inclined plane 74a.

When the fragile portion 156 is broken and the lock depressed portion (second lock portion) 152 is disengaged from the lock pin (first lock portion) 74 under the stress applied around the longitudinal axis L onto the cover 14 attached to the distal framing portion 22, the guide protruding portion (second attachment surface) 154 provided on the inner peripheral surface 102a of the cover 14 restricts the movement of the guide groove (first attachment surface) 70 of the distal framing portion 22 around the longitudinal axis L.

In addition, as shown in FIGS. 13C and 13E, the right side edge 122 is retracted into the retraction portion 220 of the jig 200. If the jig 200 is further turned with respect to the distal framing portion 22 and the cover 14 in the direction indicated by the arrow R in FIG. 12B, the user of the jig 200 needs to apply a force which would fold the right side edge 122. The support peripheral surface 214 of the jig 200 will then become resistant to sliding on the rotation peripheral surface 158 of the cover 14 around the central axis C. The user of the jig 200 will recognize this state. Thus, when the jig 200 is turned with respect to the distal framing portion 22 and the cover 14 in the direction indicated by the arrow R in FIG. 12B, the user of the jig 200 perceives a drag until the coupling portion 156c of the fragile portion 156 is broken and the engagement of the lock pin 74 and the lock depressed portion 152 is released. Thereafter, the user perceives reduction of the drag, and then the user perceives the drag again.

The first protruding portion 216 and the second protruding portion 218 are not in contact with any component of the distal framing portion 22. This prevents a load from being applied onto the distal framing portion 22 when the cover 14 is removed from the distal framing portion 22 by the jig 200.

As shown in FIG. 12B, the fragile portion 156 is exposed, even when the jig 200 is fitted to the cover 14 that is attached to the distal framing portion 22. That is, the jig 200 does not cover the fragile portion 156 and the lock depressed portion 152. This allows the user to directly observe the state of the fragile portion 156 being broken. Moreover, when the fragile portion 156 is broken by the jig 200 and the lock pin 74 is disengaged from the lock depressed portion 152, these portions are prevented from interfering with the jig 200 and from interrupting the turn and breakage operation of the jig 200.

Figure 14:
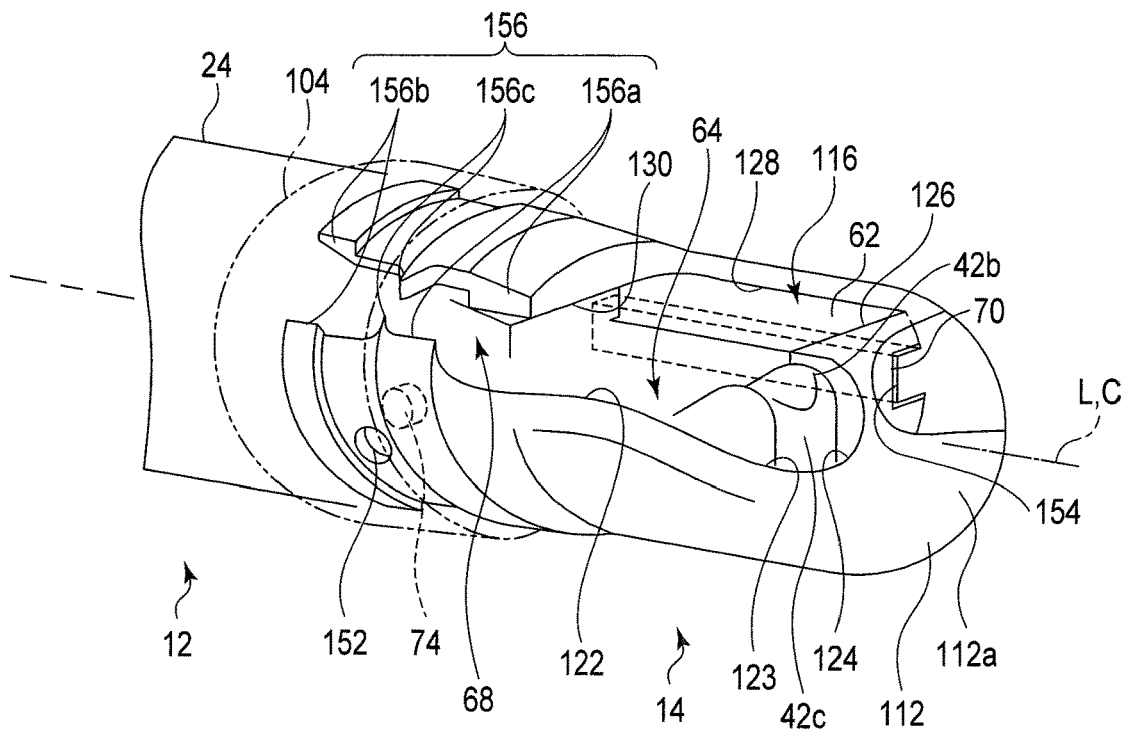
FIG. 14 is a schematic perspective view showing a state in which the coupling portion of the fragile portion is broken to remove the endoscope cover from the distal framing portion of the endoscope according to the first embodiment.

Then, as shown in FIG. 14, the jig 200 is pulled to the distal side along the longitudinal axis L from the cover 14 in which the fragile portion 156 is broken. Since the fragile portion 156 is broken, and the lock depressed portion 152 is disengaged from the lock pin 74 of the distal framing portion 22, the cover 14 may be pinched by the user's fingers, or by a forceps or the like to remove the cover 14 from the distal framing portion 22 to the distal side along the longitudinal axis L. In this manner, sanitation and safety can be ensured for users (surgeons and surgery staff).

Depending on the conditions of the breakage, the cover 14 may come off the distal framing portion 22 together with the jig 200.

The removed cover 14 (broken cover) is disposed of. The endoscope, from which the cover 14 has been removed, that is, the insertion section 12 including the distal framing portion 22, the operation section 16, and the universal cord 18, are adequately washed, disinfected, and sterilized, and provided for reuse. Then, a new cover 14 is suitably attached to the distal framing portion 22 for observation and treatment.

The jig 200 used for removal of the cover 14 from the distal framing portion 22 may also be disposed of, together with the cover 14. In this case, the cover 14 and the jig 200 may be commercially offered in packages as a cover unit. Furthermore, the endoscope 10 including the cover 14 and the jig 200 may be commercially offered in packages as an endoscope unit.

If the jig 200 holding the distal framing portion 22 is turned with respect to the distal framing portion 22 and the cover 14 in a direction opposite to the direction indicated by the arrow R in FIG. 12B, the first protruding portion 216 of the jig 200 presses the wall surface 64a of the storage portion 64 of the main body 52 of the distal framing portion 22. Further, the opposed surface 218a of the second protruding portion 218 maintains the contact with the distal side covering portion 126a of the distal side edge 126 of the cover 14. As a result, the distal framing portion 22 and the cover 14 will turn in the same direction as the jig 200. The distal framing portion 22 will therefore be prevented from receiving a load from the jig 200, and the cover 14 will not be removed from the distal framing portion 22.

As described above, the endoscope 10 according to the present embodiment realizes the following:

The disposable type cover 14 can be used for the distal framing portion 22. The cover 14 can be removed at the time of the washing of the distal framing portion 22, and therefore even the back side of the swing table 42 can be easily and reliably washed by use of a brush or the like.

When attaching the cover 14 to the distal framing portion 22, the fragile portion 156 formed by the slits 156a and 156b can be used to facilitate the elastic deformation. Moreover, the guide groove 70 and the guide protruding portion 154 facilitate the positioning of the cover 14 at a predetermined position in the turning direction (peripheral direction).

When removing the cover 14 from the distal framing portion 22, the depressed portion 124 of the open edge 116 is pressed open. At this point, the retention portions of the distal framing portion 22 and the cover 14 (i.e., the guide groove 70 of the distal framing portion 22 and the guide protruding portion 154 of the cover 14) are formed firmly enough to withstand the force in the turning direction of the longitudinal axis L. Thus, the retention portions act to maintain the engagement even under the force applied in the peripheral direction of the cover 14. The stress therefore can be concentrated in the fragile portion 156 of the cover 14, and the force for removal of the cover 14 can be concentrated to break the fragile portion 156 and disengage the lock portions (i.e., the lock pin 74 of the distal framing portion 22 and the lock depressed portion 152 of the cover 14). That is, the force for removal of the cover 14 can be concentrated at the fragile portion 156. Further, the lock depressed portion 152 of the cover 14 can be disengaged from the lock pin 74 of the distal framing portion 22 by the momentum of the stress that is released by the breakage of the coupling portion 156c of the fragile portion 156. As a result, the breakage of the fragile portion 156 and disengagement of the lock portions (the lock pin 74 of the distal framing portion 22 and the lock depressed portion 152 of the cover 14) can be performed at approximately the same time.

Here, the engagement distance of the guide protruding portion 154 of the cover 14 with the guide groove 70 of the distal framing portion 22 is set long. Thus, when breaking the cover 14 by use of the jig 200, the pressing force onto the cover 14 can be further concentrated on the breakage of the fragile portion 156 and the disengagement of the lock portions (the lock pin 74 of the distal framing portion 22 and the lock depressed portion 152 of the cover 14).

As a result, the fragile portion 156 breaks the annular portion 114 along the longitudinal axis L, and tears the cover 14 in the peripheral direction. With the fragile portion 156 being broken and the engagement of the lock depressed portion 152 with the lock pin 74 being released, the cover 14 can be easily removed from the distal framing portion 22 of the insertion section 12 along the longitudinal axis L.

The fragile portion 156 and the lock depressed portion 152 are formed at positions approximately 90° apart from each other in the peripheral direction of the longitudinal axis L. Moreover, the distal side covering portion 126a of the cover 14 is on the distal side of the flat portion 62. This regulates the movement of the distal side covering portion 126a with respect to the right side edge 122 in the peripheral direction. Thus, when the pressing force is applied to open the depressed portion 124 of the open edge 116, the distal side edge 126 maintains its position, while the right side edge 122 moves in the peripheral direction to break the fragile portion 156. At the same time, the lock depressed portion 152 can be disengaged from the lock pin 74.

In particular, the fragile portion 156 of the cover 14 is preferably formed at a position away from the guide protruding portion 154 of the cover 14 in the peripheral direction of the central axis C, or in other words, at a position close to the lock depressed portion 152. With such an arrangement, the deformation amount of the fragile portion 156 can be increased in comparison with the deformation amount of the guide protruding portion 154 of the cover 14 in the peripheral direction of the central axis C. As a result, the fragile portion 156 can be reliably broken when removing the cover 14 from the distal framing portion 22.

It should be noted that the cover 14 is often far smaller than the user's hand. When the user is removing the cover 14 using the force of the hand, the movement of the hand with respect to the cover 14 is not regulated. On the other hand, the maximum turn amount with respect to the distal framing portion 22 can be regulated by the support peripheral surface 214 of the jig 200 and the rotation peripheral surface 158 of the cover 14. By using the jig 200, the cover 14 can be removed from the distal framing portion 22 in a series of operations. The user therefore can be prevented from removing the cover 14 by excessive force of the user's hand when the jig 200 is used to remove the cover 14 from the distal framing portion 22.

The cover 14 attached to the distal framing portion 22 is configured so that when the jig 200 is adopted, the user indirectly breaks the fragile portion 156 with the jig 200 applying a stress at a position away from the fragile portion 156 (a position indicated by a reference number 123), instead of directly breaking the fragile portion 156 itself. Moreover, when the jig 200 is used, at least part of the fragile portion 156 is exposed. Therefore, the user can perform the breaking operation while directly visually observing the fragile portion 156.

Furthermore, when the cover 14 is removed from the distal framing portion 22 by use of the jig 200, the distal framing portion 22 will not be brought into contact with any position of the jig 200, from the beginning to the end of the application of stress for the removal. The jig 200 is therefore prevented from applying a load to the distal framing portion 22.

Thus, the present embodiment offers the endoscope cover 14 that can be easily removed from the distal framing portion 22 of the insertion section 12, as well as the endoscope 10 having such an endoscope cover 14, the cover unit, and the endoscope unit.

In the present embodiment, the example in which the lock pin 74 includes the inclined plane 74a has been described, but the inclined plane 74a is not necessarily required.

In the embodiment, the example in which the lock pin 74 is arranged in the distal framing portion 22 to protrude outwardly in the radial direction with the lock depressed portion 152 arranged in the inner endoscope cover 14 has been described but the arrangement of the projection and depression may be reversed. That is, a lock depressed portion may be formed in the distal framing portion 22, and a lock pin may be formed in the endoscope cover 14 to be engaged with the lock depressed portion.

In the present embodiment, the example is described as turning the jig 200 with respect to the distal framing portion 22 around the center axis C if the jig 200 is adopted to remove the cover 14 attached to the distal framing portion 22. Alternatively, when the jig 200 shown in FIGS. 15A and 15B is adopted, the jig 200 is not necessarily turned but may be simply moved along the center axis C with respect to the cover 14 attached to the distal framing portion 22.

Figure 15A:
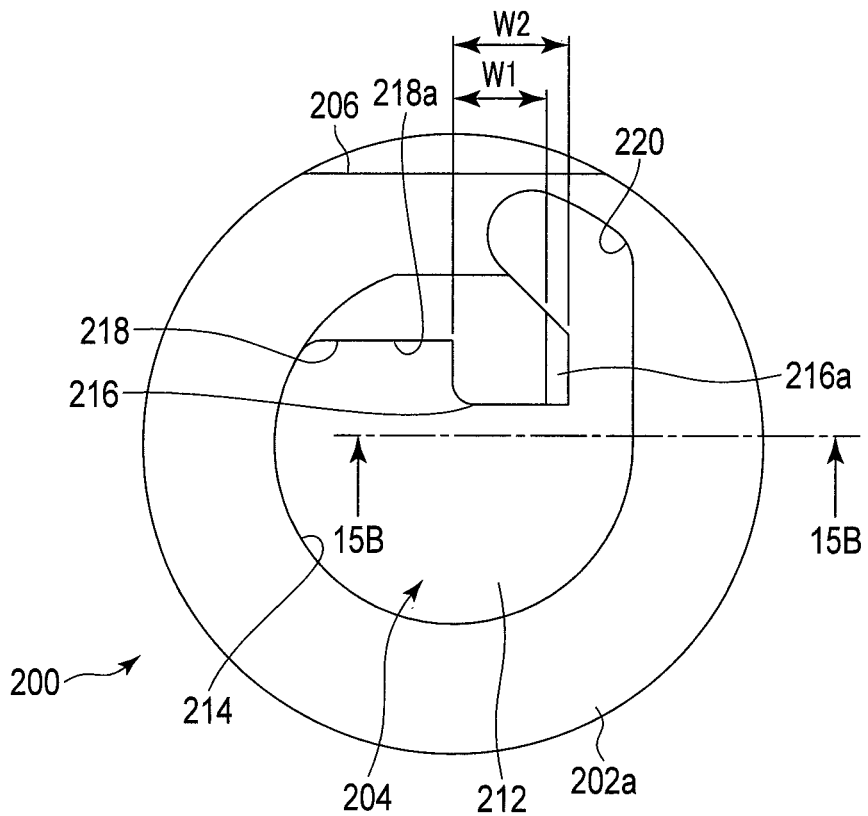
FIG. 15A is a schematic front view of an acting portion provided at one end of a jig for removing the endoscope cover that is attached to the distal framing portion of the endoscope, according to a modification of the first to third embodiments.
Figure 15B:
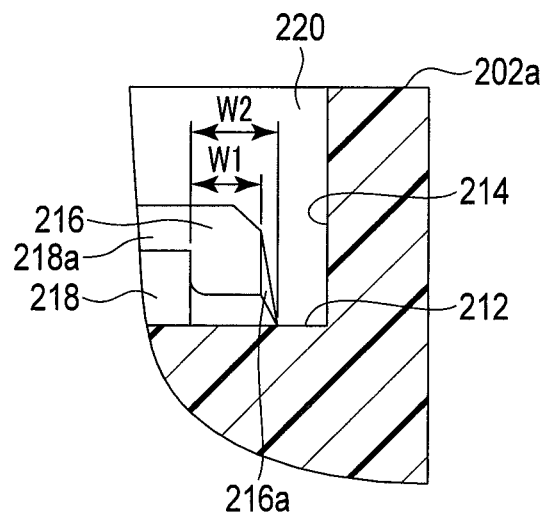
FIG. 15B is a schematic cross sectional view taken along the line 15B-15B in FIG. 15A.

In the jig 200, as shown in FIGS. 15A and 15B, the pressure portion 216a of the first protruding portion 216 in the acting portion 204 is formed as an inclined surface. The width of the pressure portion 216a of the first protruding portion 216 increases from W1 to W2 along the first protruding portion 216 from the one end 202a of the column 202 toward the bottom surface 212.

The operation using the jig 200 shown in FIGS. 15A and 15B will be briefly described.

As shown in FIG. 12A, the acting portion 204 of the jig 200 is brought to the position shown in FIG. 15B and fitted onto the distal framing portion 22 with the cover 14 attached. Here, even if the jig 200 is not turned around the axis of the central axis C, the pressure portion 216a that is formed as the inclined surface of the first protruding portion 216 presses the pressure receiving portion 123 in the peripheral direction of the central axis C. With such a structure, when the jig 200 shown in FIG. 15A is moved along the central axis C, a stress is applied to the distal framing portion 22 with the cover 14 attached around the central axis C in the same manner as turning the jig 200 of FIG. 11A around the central axis C, and the fragile portion 156 is thereby broken. At the same time as the breakage of the fragile portion 156, the engagement of the lock depressed portion 152 of the cover 14 with the lock pin 74 of the distal framing portion 22 is released.

In this case also, the guide protruding portion 154 of the cover 14 acts to maintain the engagement with the guide groove 70 of the distal framing portion 22, as described above. The guide protruding portion 154 therefore can regulate the movement of the cover main body 102 around the center axis C with respect to the distal framing portion 22.

As described above, even when the jig 200 is fitted onto the cover 14 attached to the distal framing portion 22, the fragile portion 156 is exposed. That is, the jig 200 will not cover the fragile portion 156 and the lock depressed portion 152. The user is therefore allowed to directly observe the state of the fragile portion 156. If the fragile portion 156 is not broken by the inclined pressure portion 216a, the jig 200 may then be turned around the central axis C, as described above.

Modifications of the first embodiment are now described. It should be noted that these modifications can be suitably combined.

In the example shown in FIGS. 16A and 16B, the shape of the fragile portion 156 differs from the fragile portion 156 described in the first embodiment.

As shown in FIG. 16A, the fragile portion 156 according to this modification example includes a slit 356a and a coupling portion 356b. The slit 356a is formed continuously from the proximal side edge 130 of the open edge 116. The slit 356a extends along the longitudinal axis L, up to the proximal end of the annular depressed portion 132a of the annular portion 114 (i.e., the boundary between the attachment portion 132 and the flange portion 134).

The coupling portion 356b is formed on the flange portion 134. As can be seen from FIG. 16B, the coupling portion 356b becomes thinner toward the proximal end along the longitudinal axis L. The inner diameter of the coupling portion 356b increases toward the proximal end. The coupling portion 356b is preferably tapered. It is preferable that the coupling portion 356b is slightly thinner than the skirt portion 134a of the flange portion 134.

In the example shown in FIGS. 17A and 17B, the shape of the fragile portion 156 differs from the fragile portion 156 described in the first embodiment.

As shown in FIG. 17A, the fragile portion 156 includes a first thin portion 456a, a second thin portion 456b, and a coupling portion 456c. It is preferable that, as shown in FIG. 17B, the first thin portion 456a and the second thin portion 456b are formed to be flush in the circumferential direction with the rest of the outer peripheral surface of the cover main body 102 that is adjacent to these thin portions, and that the inner peripheral surface 102a is formed into a depression. The first thin portion 456a functions in the same manner as the slit 156a described in the first embodiment. The second thin portion 456b functions in the same manner as the slit 156b described in the first embodiment.

That is, the fragile portion 156 is not provided with the slits 156a and 156b, and the first thin portion 456a, the second thin portion 456b, and the coupling portion 456c are formed by a material forming the annular portion 114. Since the first thin portion 456a and the second thin portion 456b are formed to be thinner than the rest of the portion of the annular portion 114, the first thin portion 456a and the second thin portion 456b are deformed more easily than the rest of the annular portion 114 when the annular portion 114 receives an external stress. Thus, the stress is concentrated in the first thin portion 456a, the second thin portion 456b, and the coupling portion 456c. As a result, the first thin portion 456a, the second thin portion 456b, and the coupling portion 456c can be more easily broken in a mechanical manner than the rest of the annular portion 114. In other words, the mechanical strength of the fragile portion 156, which represents the entire fragile portion including the first thin portion 456a, the second thin portion 456b, and the coupling portion 456c, is determined to be lower than the mechanical strength of the rest of the annular portion 114.

The slit 156a described in the first embodiment may of course be used in place of the first thin portion 456a, or the slit 156b described in the first embodiment may be used in place of the second thin portion 456b. This also applies to the modification examples described later.

The Example illustrated in FIG. 18 is a further modification of the example of FIG. 17A. The position and angle of the fragile portion 156 of FIG. 18 differ from the example of FIG. 17A.

As illustrated in FIG. 18, the fragile portion 156 is positioned further away from the guide protruding portion 154, in comparison with the fragile portion 156 described in the first embodiment as illustrated in FIG. 4A. The deformation amount of the fragile portion 156 can be set larger than the deformation amount of the guide protruding portion 154 of the cover 14 in the peripheral direction with respect to the central axis C.

The fragile portion 156 includes a first thin portion 556a, a second thin portion 556b, and a coupling portion 556c. It is preferable that the first thin portion 556a and the second thin portion 556b are formed to be flush in the circumferential direction with the rest of the portions of the outer peripheral surface of the cover main body 102 that are adjacent and that the inner peripheral surface 102a be formed into a depression.

The first thin portion 556a is formed at a position adjacent to the proximal side edge 130 of the open edge 116. The first thin portion 556a and the second thin portion 556b extend straight in a direction oblique to the longitudinal axis L.

The first thin portion 556a functions in the same manner as the slit 156a described in the first embodiment. The second thin portion 556b functions in the same manner as the slit 156b described in the first embodiment.

The fragile portion 156 here is positioned further away from the guide protruding portion 154 than the aforementioned fragile portion 156 of FIG. 17A. The deformation amount of the fragile portion 156 therefore can be set larger than the deformation amount of the guide protruding portion 154 of the cover 14 in the peripheral direction with respect to the central axis C.

The Example illustrated in FIG. 19 is a further modification of the examples of FIGS. 17A and 18. The position and angle of the fragile portion 156 illustrated in FIG. 19 are different from the example in FIGS. 17A and 18.

As shown in FIG. 19, the fragile portion 156 includes a first thin portion 656a, a second thin portion 656b, and a coupling portion 656c. It is preferable that the first thin portion 656a and the second thin portion 656b are formed to be flush in the circumferential direction with the rest of the outer peripheral surface of the cover main body 102 that is positioned adjacent, and that the inner peripheral surface 102a is formed into a depression.

The first thin portion 656a is formed at a position adjacent to the right side edge 122 of the open edge 116. The second thin portion 656b extends straight along the longitudinal axis L.

The first thin portion 656a functions in the same manner as the slit 156a described in the first embodiment. The second thin portion 656b functions in the same manner as the slit 156b described in the first embodiment.

The fragile portion 156 is positioned further away from the guide protruding portion 154 than the fragile portion 156 in the aforementioned modification example of FIG. 17A. The deformation amount of the fragile portion 156 therefore can be set larger than the deformation amount of the guide protruding portion 154 of the cover 14 in the peripheral direction with respect to the central axis C.

In the example shown in FIGS. 20A and 20B, the cover main body 102 and the presser ring 104 (see FIG. 4A) are not separate bodies, but are formed in an integral unit. In this modification example, the presser ring 104 made of a rubber material is not included.

As shown in FIGS. 20A and 20B, the fragile portion 156 of the cover main body 102 includes a slit 756a, a thin portion 756b, and a coupling portion 756c. The coupling portion 756c is formed between the slit 756a and the thin portion 756b. It is preferable that the thin portion 756b is continuous with the proximal end 114a of the cover main body 102. In addition, it is preferable that the lock depressed portion 152 is depressed with respect to the inner peripheral surface 102a of the cover main body 102. Thus, even when the cover main body 102 is formed integrally with the presser ring 104, the cover 14 shown in FIG. 20A can be used in the same manner as the cover 14 described in the first embodiment (see FIG. 5A).

Next, the second embodiment will be described with reference to FIGS. 21A to 22B. This embodiment is a modification of the first embodiment including its modification examples, and the same reference numerals are given to the same components as described in the first embodiment or components having the same function, and a detailed description of these components is omitted.

Figure 21A:
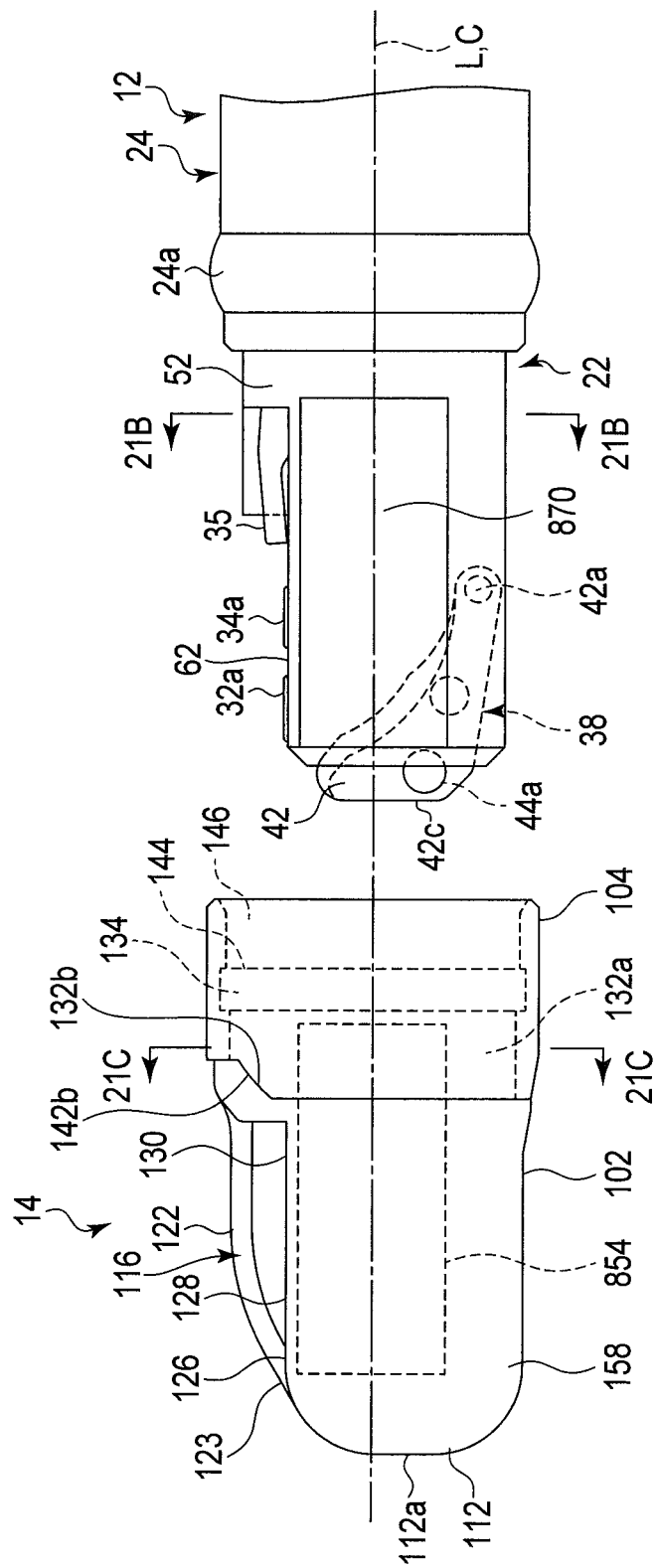
FIG. 21A is a schematic side view showing the state of the endoscope cover being attached to the distal framing portion of the endoscope according to the second embodiment.
Figure 21B:
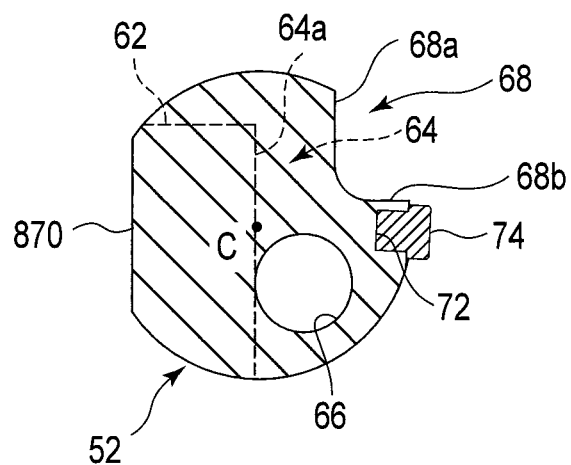
FIG. 21B is a schematic cross sectional view of the distal framing portion of the endoscope according to the second embodiment, taken along the line 21B-21B in FIG. 21A.
Figure 21C:
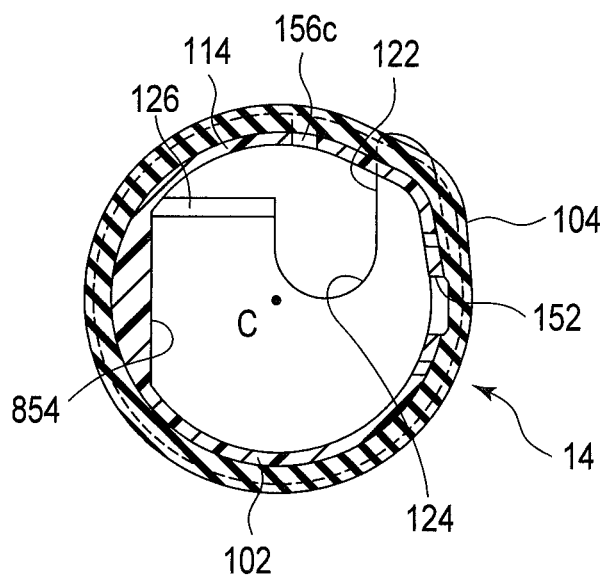
FIG. 21C is a schematic cross sectional view of the distal framing portion of the endoscope according to the second embodiment, taken along the line 21C-21C in FIG. 21A.

As illustrated in FIGS. 21A and 21B, a first attachment surface (first restriction portion) 870 is formed on the outer peripheral surface of the main body 52 of the distal framing portion 22, in place of the guide groove 70 (see FIG. 6) described in the first embodiment. As illustrated in FIGS. 21A and 21C, a second attachment surface (second restriction portion) 854 is formed on the inner peripheral surface 102a of the cover 14, in place of the guide protruding portion 154 (see FIG. 6) described in the first embodiment, to be engaged with the first attachment surface 870. The first attachment surface 870 of FIGS. 21A and 21B and the second attachment surface 854 of FIGS. 21A and 21C are preferably both formed into flat surfaces. The first attachment surface 870 and the second attachment surface 854 are formed to have approximately the same shape and size. In this manner, the displacement of the cover 14 with respect to the distal framing portion 22 can be avoided.

When the cover 14 is attached to the distal framing portion 22, the first attachment surface 870 and the second attachment surface 854 are brought into contact with each other, as shown in FIGS. 22A and 22B. The second attachment surface 854 regulates the movement of the cover 14 with respect to the distal framing portion 22 around the longitudinal axis L at the time of attaching the cover 14 to the distal framing portion 22.

In a state that the cover 14 is attached to the distal framing portion 22 when stress is applied to the cover 14 around the longitudinal axis L to break the fragile portion 156 and to also release the engagement of the second lock portion 152 with the first lock portion 74, the second attachment surface 854 provided in the inner peripheral surface 102a of the cover 14 regulates the movement with respect to the first attachment surface 870 of the distal framing portion 22 around the longitudinal axis L. When the force is applied to the cover 14 around the longitudinal axis L with the cover main body 102 attached to the distal framing portion 22, the bearing force of the second attachment surface 854 is determined so that the bearing force is greater than the total of the amount of force that would break the fragile portion 156 and the amount of force that would release the engagement of the lock depressed portion 152 with the lock pin 74. For this reason, the fragile portion 156 can be broken by use of, for example, the jig 200 (see FIGS. 11A and 15A), while maintaining the engagement of the first attachment surface 870 with the second attachment surface 854.

Next, the third embodiment will be described with reference to FIGS. 23A and 23B. This embodiment is a modification of the first and second embodiments including its modification examples, and the same reference numerals are given to the same components as described in the first and second embodiments or the components having the same function, and a detailed description thereof is omitted.

Figure 23A:
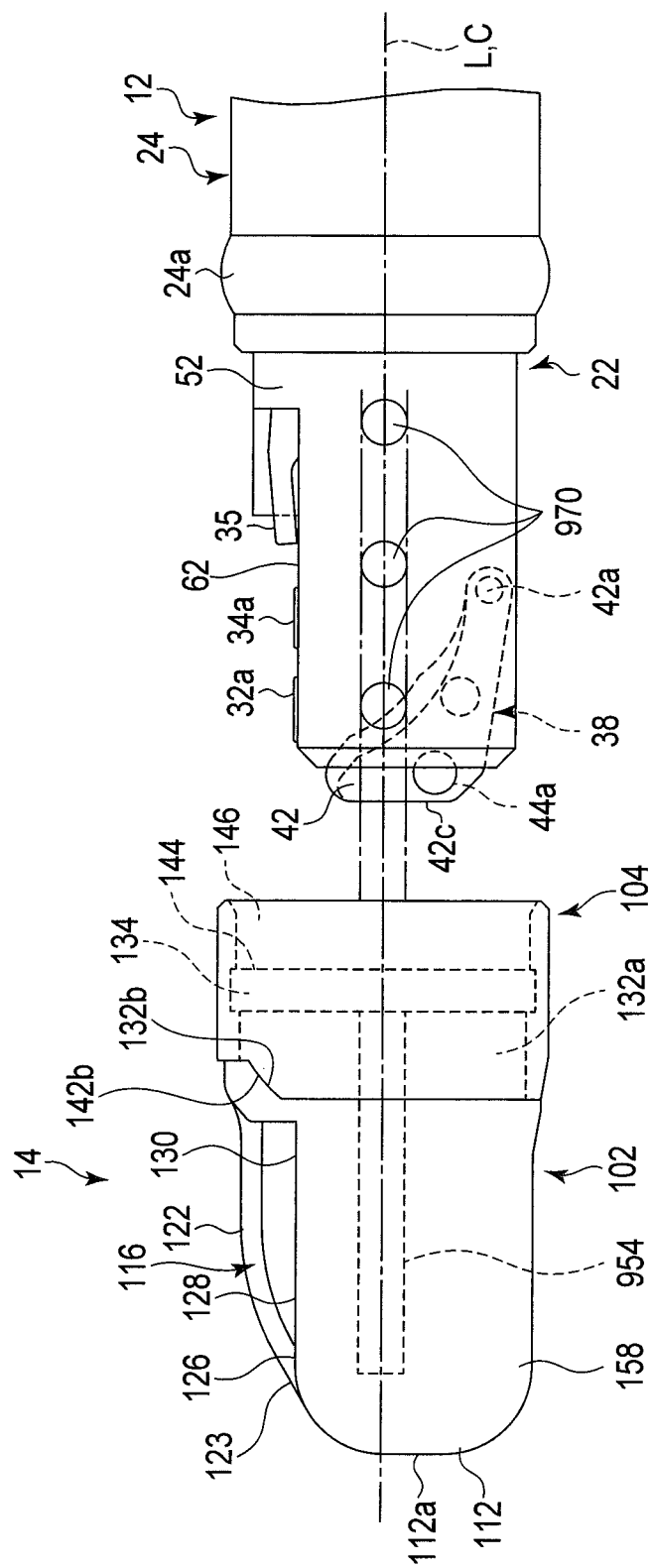
FIG. 23A is a schematic side view showing the state of the endoscope cover that is being attached to the distal framing portion of the endoscope according to a third embodiment.
Figure 23B:
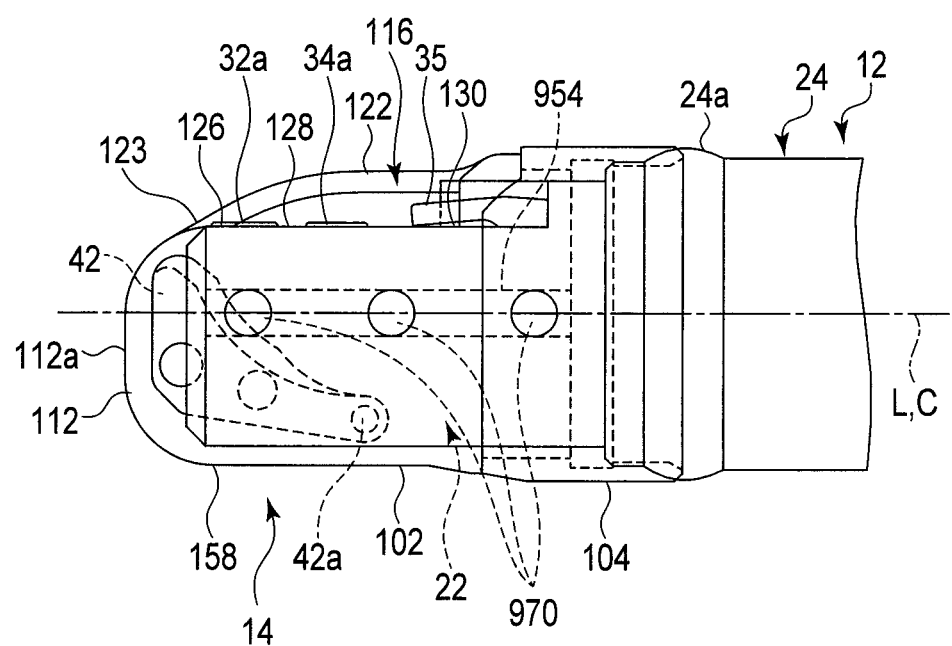
FIG. 23B is a schematic side view showing the state of the endoscope cover that has been attached to the distal framing portion of the endoscope according to the third embodiment.

As illustrated in FIG. 23A, multiple protrusions (first restriction portion) 970 are formed on the outer peripheral surface of the main body 52 of the distal framing portion 22, in place of the guide groove 70 described in the first embodiment (see FIG. 6). The protrusions 970 are arranged at suitable intervals along the longitudinal axis L. A guide groove (second restriction portion) 954 is formed in the inner peripheral surface 102a of the cover main body 102 of the cover 14 to guide the protrusions 970, in place of the guide protruding portion 154 described in the first embodiment (see FIG. 6).

The protrusions 970 and the guide groove 954 regulate the movement of the cover 14 around the longitudinal axis L of the distal framing portion 22 when attaching the cover 14 to the distal framing portion 22. In this manner, the displacement of the cover 14 with respect to the distal framing portion 22 in the peripheral direction can be avoided.

In a state that the cover 14 is attached to the distal framing portion 22 when the stress is applied to the cover 14 around the longitudinal axis L to break the fragile portion 156 and to release the engagement of the second lock portion 152 with the first lock portion 74, the guide groove 954 formed in the inner peripheral surface 102*a* of the cover 14 regulates the movement of the protrusions 970 of the distal framing portion 22 around the longitudinal axis L. When the force is applied to the cover 14 around the longitudinal axis L with the cover 14 attached to the distal framing portion 22, the bearing force of the guide groove 954 is determined so that the bearing force is greater than the total of the amount of force that would break the fragile portion 156 and the amount of force that would release the engagement of the second lock portion 152 with the first lock portion 74.

Thus, the fragile portion 156 can be broken by use of, for example, the jig 200 (see FIGS. 11A and 15A), with the protrusions 970 arranged in the guide groove 954.

In the first to third embodiments described above, the normal line N (see FIGS. 2C, 3B, and 3C) to the flat portion 62 in which the illumination window 32*a* and the observation window 34*a* are provided is indicated in the direction substantially orthogonal to the longitudinal axis L. The direction of the normal line N to the flat portion 62, however, can be suitably determined. If the direction of the normal line N is suitably determined, the shape of the acting portion 204 of the jig 200 can be suitably determined.

According to the first to third embodiments described above, the distal framing portion 22 is of a side-viewing type. Alternatively, the distal framing portion 22 may be formed of a so-called direct-viewing type, with which an observation is conducted in the direction along the longitudinal axis L of the insertion section 12, or of a so-called oblique-viewing type, with which an observation is conducted in a suitable direction between the direction along the longitudinal axis L of the insertion section 12 and the direction orthogonal to the longitudinal axis L.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cover unit comprising:
   an endoscope cover comprising:
      a cover main body configured to be attached to a distal framing portion of an insertion section of an endoscope along a longitudinal axis of the insertion section, the cover main body comprising:
         an annular portion configured to surround a periphery of the distal framing portion; and
         an open edge;
      a fragile portion at least a part of which is provided in the annular portion of the cover main body, the fragile portion having a mechanical strength lower than a rest of the annular portion; and
      a restriction portion configured to regulate movement of the cover main body around the longitudinal axis with respect to the distal framing portion when an intended stress is applied to the cover main body around the longitudinal axis with the cover main body attached to the distal framing portion and the fragile portion is broken;
   a lock portion configured to engage the cover main body with the distal framing portion; and
   a jig configured to remove the endoscope cover, which is in a state of being attached to the distal framing portion, from the distal framing portion,
   wherein in a state that the cover main body is attached to the distal framing portion, the jig is configured to break the fragile portion and is configured to release the engagement of the lock portion with the distal framing portion, by applying the intended stress onto the open edge around the longitudinal axis, while the restriction portion of the endoscope cover maintains a state in which movement of the restriction portion with respect to the distal framing portion is regulated around the longitudinal axis.

2. The cover unit according to claim 1, wherein a breaking stress of the restriction portion under application of a force to the distal framing portion around the longitudinal axis is greater than a total of an amount of force that breaks the fragile portion and an amount of force that releases the engagement of the lock portion with the distal framing portion.

3. The cover unit according to claim 1, wherein the restriction portion regulates the movement of the cover main body around the longitudinal axis of the distal framing portion when the cover main body is attached to the distal framing portion.

4. The cover unit according to claim 1, wherein a position of the restriction portion differs from a position of the lock portion with respect to a peripheral direction around the longitudinal axis.

5. The cover unit according to claim 4, wherein in a state that the cover main body is attached to the distal framing portion, when the endoscope is viewed in a section perpendicular to the longitudinal axis, and the section is divided into a first region and a second region that are different from each other, the lock portion is positioned in the first region, and the restriction portion is positioned in the second region.

6. The cover unit according to claim 1, wherein:
   the open edge is configured to expose a swing table of a swing mechanism arranged in the distal framing portion through the open edge to outside, and is configured to expose an observation optical system through the open edge, and
   the fragile portion is arranged at a position on a proximal side of the open edge where the swing table is provided along the longitudinal axis.

7. An endoscope unit comprising:
   the cover unit according to claim 1; and
   the distal framing portion of the insertion section of the endoscope, the cover unit being attached to the distal framing portion along the longitudinal axis of the insertion section.

8. The endoscope unit according to claim 7, wherein:
   the distal framing portion includes a part of a swing mechanism which is configured to swing a treatment instrument at a distal end of the insertion section, and
   the open edge is configured to expose a swing table of the swing mechanism through the open edge to outside.

9. The endoscope unit according to claim 8, wherein:
   the restriction portion regulates movement of the cover main body with respect to the distal framing portion around the longitudinal axis of the insertion section when engagement of the lock portion with the distal framing portion is released,
   the distal framing portion includes an other lock portion to be engaged with the lock portion and an other restriction portion to be engaged with the restriction portion, and
   in a state that the cover main body is attached to the distal framing portion when the distal framing portion and the endoscope cover are viewed in a section perpendicular to the longitudinal axis, and the section is divided into a first region and a second region that are adjacent to each other, the other lock portion and the swing mechanism are arranged adjacent to each other in the first region, and the other restriction portion is arranged in the second region, away from the other lock portion.

10. The endoscope unit according to claim 9, wherein:
the other restriction portion includes a first guide in the distal framing portion, and
the restriction portion includes a second guide in the cover main body to move with respect to the first guide along the longitudinal axis.

11. The endoscope unit according to claim 10, wherein:
the first guide is a groove along the longitudinal axis, and
the second guide includes a protruding portion that protrudes from an inner peripheral surface of the cover main body to engage with the first guide.

12. The endoscope unit according to claim 7, wherein:
the distal framing portion is provided with a part of a swing mechanism configured to swing a treatment tool at a distal end of the insertion section,
the open edge is configured to expose a swing table of the swing mechanism through the open edge to outside, and
in a state that the cover main body is attached to the distal framing portion, the jig breaks the fragile portion and releases the engagement of the lock portion with the distal framing portion, by applying an intended stress onto the open edge around the longitudinal axis, while the restriction portion maintains a state in which movement of the restriction portion with respect to the distal framing portion is regulated around the longitudinal axis.

* * * * *